(12) United States Patent
Bogran et al.

(10) Patent No.: US 11,957,167 B2
(45) Date of Patent: Apr. 16, 2024

(54) CONTAINER FOR ELECTRONIC VAPORIZER DEVICE

(71) Applicant: Philip Morris Products, S.A., Neuchâtel (CH)

(72) Inventors: Jon Bogran, Kenner, LA (US); Matthew Greenfield, Scotts Valley, CA (US); Peter Nysen, San Jose, CA (US); Neeraj S. Bhardwaj, Belmont, CA (US); Andrew L. Bleloch, Kenmore, WA (US)

(73) Assignee: Philip Morris Products, S.A., Neuchâtel (CH)

( * ) Notice: Subject to any disclaimer, the term of this patent is extended or adjusted under 35 U.S.C. 154(b) by 920 days.

(21) Appl. No.: 16/971,109

(22) PCT Filed: Feb. 7, 2019

(86) PCT No.: PCT/US2019/017045
§ 371 (c)(1),
(2) Date: Aug. 19, 2020

(87) PCT Pub. No.: WO2019/157177
PCT Pub. Date: Aug. 15, 2019

(65) Prior Publication Data
US 2021/0378304 A1 Dec. 9, 2021

Related U.S. Application Data

(60) Provisional application No. 62/627,870, filed on Feb. 8, 2018.

(51) Int. Cl.
*A24F 40/42* (2020.01)
*A24F 40/10* (2020.01)
(Continued)

(52) U.S. Cl.
CPC .............. *A24F 40/42* (2020.01); *A24F 40/10* (2020.01); *A24F 40/44* (2020.01); *A24F 40/465* (2020.01); *A24F 40/485* (2020.01); *H05B 6/108* (2013.01)

(58) Field of Classification Search
None
See application file for complete search history.

(56) References Cited

U.S. PATENT DOCUMENTS

2011/0108031 A1    5/2011  Korneff et al.
2014/0060554 A1*   3/2014  Collett .................. A24F 40/46
                                              392/386
(Continued)

FOREIGN PATENT DOCUMENTS

CN    105307526 A    2/2016
CN    107105791 A    8/2017
(Continued)

OTHER PUBLICATIONS

Chinese Office Action mailed on Jan. 11, 2024 issued in Chinese Patent Application No. 201980018384.0 filed on Feb. 7, 2019, with English Translation, total 24 pages.

*Primary Examiner* — Tho D Ta
(74) *Attorney, Agent, or Firm* — Oblon, McClelland, Maier & Neustadt, L.L.P.

(57) ABSTRACT

Provided is a cartridge assembly for containment of a vaporizable substance to be used in an electronic vaporizer device. The cartridge assembly includes a cartridge and a susceptor element. The cartridge includes a base section and a side section coupled to the base section at a first end of the side section. An aperture is defined at a second end of the side section and the side section includes at least two apertures located in the side section, where the at least two apertures are configured to allow air to flow into an interior (Continued)

chamber of the cartridge when air flows out of the aperture defined at the second end. The susceptor element is located within the cartridge.

18 Claims, 16 Drawing Sheets

(51) Int. Cl.
*A24F 40/44* (2020.01)
*A24F 40/465* (2020.01)
*A24F 40/485* (2020.01)
*H05B 6/10* (2006.01)

(56) References Cited

U.S. PATENT DOCUMENTS

| | | | |
|---|---|---|---|
| 2014/0091083 | A1 | 4/2014 | McGarvey |
| 2015/0245669 | A1 | 9/2015 | Cadieux et al. |
| 2015/0320116 | A1* | 11/2015 | Bleloch .................. A24F 40/44 |
| | | | 219/628 |
| 2017/0055584 | A1 | 3/2017 | Blandino et al. |
| 2017/0079326 | A1 | 3/2017 | Mironov |
| 2017/0202266 | A1 | 7/2017 | Sur |
| 2017/0231276 | A1* | 8/2017 | Mironov .............. H05B 1/0244 |
| | | | 131/328 |
| 2018/0027883 | A1* | 2/2018 | Zuber .................. H05B 1/0244 |
| 2018/0027884 | A1* | 2/2018 | Zuber ............... A61M 15/0036 |

FOREIGN PATENT DOCUMENTS

| | | | |
|---|---|---|---|
| EP | 3183979 | A1 | 6/2017 |
| KR | 20170007267 | A * | 1/2017 |
| WO | 2008017575 | A1 | 2/2008 |
| WO | 2017032695 | A1 | 3/2017 |
| WO | 2017129613 | A1 | 8/2017 |

* cited by examiner

CONTAINER FOR ELECTRONIC VAPORIZER DEVICE

CROSS REFERENCE AND RELATED APPLICATIONS

This application is the United States national phase of International Application No. PCT/US2019/017045 filed Feb. 7, 2019, and claims priority to U.S. Provisional Application No. 62/627,870 filed Feb. 8, 2018, the disclosures of which are hereby incorporated by reference in their entirety.

BACKGROUND

1. Field

This disclosure relates generally to systems, devices, products, apparatuses, and methods that are used in electronic vaporizer device, and, in one particular embodiment, to a container for a substance to be used in an electronic vaporizer device.

2. Technical Considerations

Induction heating includes heating an object that is electrically conductive (e.g., a metal object) by electromagnetic induction. For example, induction heating may include heating the object based on heat generated in the object by eddy currents that flow in the object. In some instances, an induction heating system may include an induction heating element and an electrically conductive object to be heated based on electromagnetic induction. The induction heating element may include an electromagnet and an electronic oscillator that passes an alternating current (AC) through the electromagnet so that the electromagnet may produce an electromagnetic field (e.g., an electromagnetic induction field). The electromagnetic field may be directed at the electrically conductive object and the electromagnetic field may penetrate the electrically conductive object. Electric currents may be generated inside the electrically conductive object based on the electromagnetic field. The electric currents may be referred to as eddy currents. The eddy currents may flow through the electrically conductive object and cause heat to be generated in the electrically conductive object based on Joule heating. In some instances, the electrically conductive object may include a ferromagnetic material (e.g., iron) and heat may be generated in the electrically conductive object based on magnetic hysteresis (e.g., magnetic hysteresis losses).

In some instances, the electrically conductive object may include a susceptor. The susceptor may be a material that has the ability to absorb electromagnetic energy and convert the electromagnetic energy to heat. The electromagnetic energy may include radiation (e.g., electromagnetic radiation) in the radio frequency spectrum or microwave spectrum. In some examples, the susceptor may be designed to emit the heat as radiation (e.g., infrared thermal radiation).

SUMMARY

Devices for, systems for, products for, apparatuses for, and/or methods for use of a container for a substance to be used in an electronic vaporizer device are disclosed that overcome some or all of the deficiencies of the prior art.

Embodiments or aspects are set forth in the following numbered clauses:

Clause 1: An electronic vaporizer device comprising: a cartridge configured to hold a vaporizable substance, the cartridge comprising: a base section; a side section coupled to the base section at a first end of the side section, wherein an aperture is defined at a second end of the side section; wherein the side section comprises one or more apertures located in the side section, the one or more apertures being configured to allow air to flow into an interior of the cartridge when air flows out of the aperture defined at the second end; wherein the base section and the side section define a fluid reservoir; a susceptor element located within the cartridge; and an induction heating element inductively coupled to the susceptor element and not in contact with the susceptor element.

Clause 2: The electronic vaporizer device of clause 1, wherein the cartridge is positioned such that the induction heating element surrounds at least a portion of the cartridge and surrounds at least a portion of the susceptor element.

Clause 3: The electronic vaporizer device of clause 1 or 2, further comprising: a power source electrically connected to the induction heating element; wherein the susceptor element is configured to heat t vaporizable substance located in the fluid reservoir based on induction heating of the susceptor element by the induction heating element; wherein the susceptor element is located in the fluid reservoir and is configured to transfer the vaporizable substance from the fluid reservoir based on a capillary action of the susceptor element; and wherein the induction heating element receives an alternating current from the power source and creates an electromagnetic field around the susceptor element, and wherein the susceptor element generates heat based on the electromagnetic field.

Clause 4: The electronic vaporizer device of any of clauses 1-3, wherein the one or more apertures are configured to allow a volume of air into an interior chamber of the cartridge, and wherein the volume of air is based on a volume per unit length of the cartridge.

Clause 5: The electronic vaporizer device of any of clauses 1-4, wherein the susceptor element comprises a plurality of wire strands that are wound together in a helical formation, wherein the wire strands comprise a ferromagnetic material.

Clause 6: The electronic vaporizer device of any of clauses 1-5, further comprising a shielding element, wherein the shielding element is located within the cartridge, and wherein the susceptor element is located within the shielding element.

Clause 7: The electronic vaporizer device of any of clauses 1-6, wherein the shielding element surrounds a portion of the susceptor element when the susceptor element is located within the shielding element.

Clause 8: The electronic vaporizer device of any of clauses 1-7, wherein the one or more apertures comprises a first aperture and a second aperture, wherein the first aperture is adjacent the second end of the side section and the second aperture is adjacent the first aperture, wherein the second aperture is vertically offset and horizontally offset from the first aperture, and wherein the first aperture is smaller than the second aperture.

Clause 9: The electronic vaporizer device of any of clauses 1-8, wherein the one or more apertures comprises a third aperture, wherein the third aperture is adjacent the second end of the side section and opposite the first aperture, and wherein the third aperture is smaller than the second aperture.

Clause 10: The electronic vaporizer device of any of clauses 1-9, wherein the one or more apertures comprises a fourth aperture, wherein the fourth aperture is adjacent the first aperture and the third aperture, and wherein the fourth aperture is larger than the first aperture and the third aperture.

Clause 11: The electronic vaporizer device of any of clauses 1-10, wherein the cartridge has a cylindrical shape.

Clause 12: The electronic vaporizer device of any of clauses 1-11, wherein the one or more apertures comprises a plurality of slit apertures located in the side section, wherein a size of an opening of the plurality of slit apertures is greater at a location adjacent the base section of the cartridge than a size of the opening of the plurality of slit apertures adjacent the second end of the side section.

Clause 13: A cartridge assembly for containment of a vaporizable substance to be used in an electronic vaporizer device comprising: a cartridge comprising: a base section; a side section coupled to the base section at a first end of the side section, wherein an aperture is defined at a second end of the side section; and wherein the side section comprises at least two apertures located in the side section, where the at least two apertures are configured to allow air to flow into an interior chamber of the cartridge when air flows out of the aperture defined at the second end; and a susceptor element located within the cartridge.

Clause 14: The cartridge assembly of clause 13, wherein the one or more apertures is configured to allow a volume of air into the interior chamber of the cartridge, and wherein the volume of air is based on a volume per unit length of the cartridge.

Clause 15: The cartridge assembly of clause 13 or 14, wherein the at least two apertures comprise a first aperture and a second aperture, wherein the first aperture is adjacent the second end of the side section and the second aperture is adjacent the first aperture, wherein the second aperture is vertically offset and horizontally offset from the first aperture, and wherein the first aperture is smaller than the second aperture.

Clause 16: The cartridge assembly of any of clauses 13-15, wherein the susceptor element comprises a plurality of wire strands that are wound together in a helical formation, and wherein the wire is a ferromagnetic material.

Clause 17: The cartridge assembly of any of clauses 13-16, wherein the susceptor element comprises a wire having a coating of at least one of zirconia, silicon dioxide, or alumina.

Clause 18: The cartridge assembly of any of clauses 13-17, further comprising a shielding element, wherein the shielding element is located within the cartridge, and wherein the susceptor element is located within the shielding element, wherein the susceptor element comprises a first ferromagnetic material and the shielding element comprises a second ferromagnetic material, and wherein the first ferromagnetic material has greater ferromagnetic properties than the second ferromagnetic material.

Clause 19: A cartridge assembly for containment of a vaporizable substance to be used in an electronic vaporizer device comprising: a cartridge comprising: a base section; a side section coupled to the base section at a first end of the side section, wherein an aperture is defined at a second end of the side section; and wherein the side section comprises one or more apertures located in the side section, wherein the one or more apertures are configured to allow air to flow into an interior chamber of the cartridge when air flows out of the aperture defined at the second end.

Clause 20: The cartridge assembly of clause 19, wherein the one or more apertures is configured to allow a volume of air into the interior chamber of the cartridge, and wherein the volume of air is based on a volume per unit length of the cartridge.

Clause 21: The cartridge assembly of clauses 19 or 20, further comprising a susceptor element located within the cartridge.

Clause 22: The cartridge assembly of any of clauses 19-21, wherein the susceptor element comprises a wire having a coating of at least one of zirconia, silicon dioxide, or alumina.

Clause 23: The cartridge assembly of any of clauses 19-22, wherein the susceptor element comprises a plurality of wire strands that are wound together in a helical formation, and wherein each strand of the plurality of wire strands comprises a ferromagnetic material.

Clause 24: The cartridge assembly of any of clauses 19-23, further comprising a shielding element, wherein the shielding element is located within the cartridge, and wherein the susceptor element is located within the shielding element.

Clause 25: The cartridge assembly of any of clauses 19-24, the shielding element surrounds a portion of the susceptor element when the susceptor element is located within the shielding element.

Clause 26: The cartridge assembly of any of clauses 19-25, wherein the one or more apertures comprises a first aperture and a second aperture, wherein the first aperture is adjacent the second end of the side section and the second aperture is adjacent the first aperture, wherein the second aperture is vertically offset and horizontally offset from the first aperture, and wherein the first aperture is smaller than the second aperture.

Clause 27: The cartridge assembly of any of clauses 19-26, wherein the one or more apertures comprises a third aperture, wherein the third aperture is adjacent the second end of the side section and opposite the first aperture, and wherein the third aperture is smaller than the second aperture.

Clause 28: The cartridge assembly of any of clauses 19-27, wherein the one or more apertures comprises a fourth aperture, wherein the fourth aperture is adjacent the first aperture and the third aperture, and wherein the fourth aperture is larger than the first aperture and the third aperture.

Clause 29: The cartridge assembly of any of clauses 19-28, wherein the cartridge has a cylindrical shape.

Clause 30: The cartridge assembly of any of clauses 19-29, wherein the one or more apertures comprises a plurality of slit apertures located in the side section, wherein a size of an opening of the plurality of slit apertures is greater at a location adjacent the base section of the cartridge than the size of the opening of the plurality of slit apertures adjacent the second end of the side section.

These and other features and characteristics of embodiments of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure. As used in the specification and the claims, the singular form of "a," "an," and "the" include plural referents unless the context clearly dictates otherwise.

BRIEF DESCRIPTION OF THE DRAWINGS

Additional advantages and details of the present disclosure are explained in greater detail below with reference to the exemplary embodiments that are illustrated in the accompanying schematic figures, in which.

DETAILED DESCRIPTION

Figure 1:
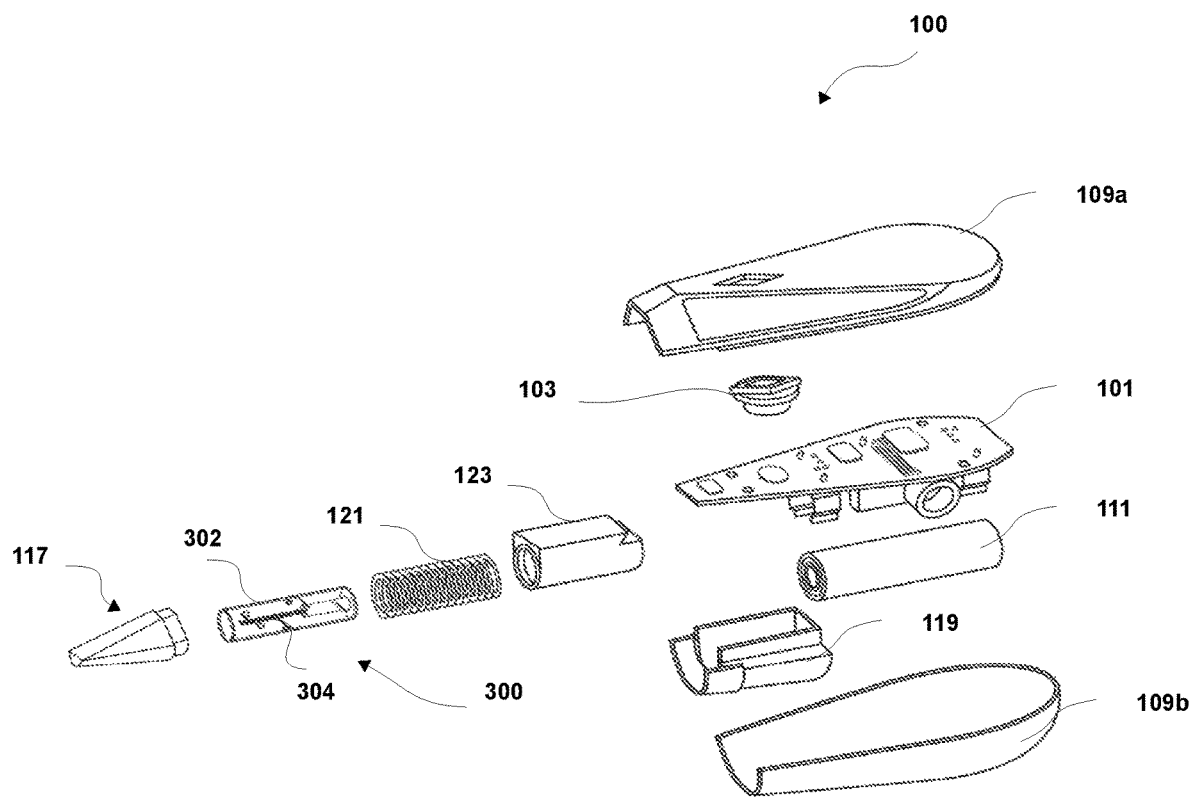
FIG. 1 is a diagram of a non-limiting embodiment of an electronic vaporizer device according to the present disclosure.

For purposes of the description hereinafter, the terms "end," "upper," "lower," "right," "left," "vertical," "horizontal," "top," "bottom," "lateral," "longitudinal," and derivatives thereof shall relate to the disclosure as it is oriented in the drawing figures. However, it is to be understood that the disclosure may assume various alternative variations and step sequences, except where expressly specified to the contrary. It is also to be understood that the specific devices and processes illustrated in the attached drawings, and described in the following specification, are simply exemplary embodiments or aspects of the disclosure. Hence, specific dimensions and other physical characteristics related to the embodiments or aspects of the embodiments disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

In some non-limiting embodiments, an induction heating system may include an induction heating element and a cartridge with a susceptor element located within the cartridge. The induction heating system may be used to heat an object that is located within the cartridge and is in thermal contact with the susceptor element (e.g., adjacent or in contact with the susceptor element so that an object can be heated by the susceptor element). For example, an electronic vaporizer device (e.g., an electronic cigarette, a personal vaporizer (PV), an electronic nicotine delivery system (ENDS), etc.), may include the induction heating system and the induction heating system may be used to heat a vaporizable substance (e.g., an organic material that produces a vapor or aerosol when heated, a vaping material, etc.) that is located within the cartridge and is in thermal contact with the susceptor element. In some non-limiting embodiments, the cartridge may have an open end in which air is drawn into an interior of the cartridge and drawn out of the interior of the cartridge.

However, by allowing air to be drawn into and out of the open end of the cartridge, the flow of air into and out of the interior of the cartridge may be restricted. For example, in a vaporizer device, an induction heating system may be compact and the size of a device, such as a thermocouple, a silicon sensor chip, and/or an infrared thermometer, may prevent the device from being used to sense the temperature of the susceptor because the device cannot be in thermal contact with the susceptor. Furthermore, the device may not be able to be in thermal contact with the susceptor and to withstand the temperature of the susceptor. In addition, the device may not be able to accurately sense the temperature of the susceptor based on the device not being able to be in thermal contact with the susceptor.

Embodiments of the present disclosure allow for improved flow of air into an interior of the cartridge and/or airflow around a susceptor element of an electronic vaporizer device. Embodiments of the present disclosure may provide a better experience in the form of improved flavor of vapor provided by the electronic vaporizer device as compared to a cartridge that does not include apertures as described in the present disclosure. Further, fewer thermal degradation byproducts may be produced based on heating a vaporizable substance. This may be, for example, because the vaporizable substance is exposed to a narrower range of temperatures (e.g., a specified temperature to which the vaporizable substance is heated by the susceptor element and may be achieved without exposing any of the vaporizable substance to temperatures significantly above that temperature) and/or faster heating of the vaporizable substance.

Referring now to FIG. 1, FIG. 1 is a disassembled view of an electronic vaporizer device 100. As shown in FIG. 1, electronic vaporizer device 100 may include upper housing 109a and lower housing 109b. As further shown in FIG. 1, the electronic vaporizer device 100 may include electronic control components 101, at least one activation button 103, cartridge assembly 300, power source 111, and mouthpiece component 117. Cartridge assembly 300 may include cartridge 302 and susceptor element 304 located within cartridge 302.

In some non-limiting embodiments, electronic vaporizer device 100 may include internal chassis 119, induction heating element 121, such as an induction coil, and a heating element body 123. As shown in FIG. 1, heating element body 123 may be sized and configured to hold induction heating element 121 when induction heating element 121 is positioned within the heating element body 123. Internal chassis 119 may be sized and configured to hold induction heating element 121 and heating element body 123 in proximity to the electronic control components 101. In this way, internal chassis 119 may allow for a compact size and control of induction heating element 121 with electronic control components 101. In some non-limiting embodiments, heating element body 123 may act as an insulator to the heat generated by induction heating of susceptor element 304 within cartridge 302 and may also shield electronic components from an electromagnetic field generated by induction heating element 121. In some non-limiting embodiments, induction heating element 121 may provide an electromagnetic field that has a frequency in the range of 50 kHz to 150 kHz when electronic vaporizer device 100 is in use. In one example, induction heating element 121 may provide an electromagnetic field that has a frequency of 100 kHz.

In some non-limiting embodiments, cartridge 302 may be sized and configured to fit within induction heating element 121, which allows for compact construction of electronic vaporizer device 100. In some non-limiting embodiments, induction heating element 121 may receive an alternating current from power source 111 and induction heating element 121 may create an electromagnetic field around susceptor element 304 located in cartridge 302. Cartridge 302 may include an aperture at one end (e.g., an open end) that allows a vapor or an aerosol from the vaporizable substance to flow out of the cartridge 302. In some non-limiting embodiments, cartridge 302 includes a reservoir. The reservoir may hold a vaporizable substance. The induction heating element 121 may be sized and configured to be housed within heating element body 123. In some non-limiting embodiments, cartridge 302 may be located entirely within induction heating element 121 or only a portion of cartridge 302 may be within induction heating element 121.

In some non-limiting embodiments, cartridge 302 may be a replaceable and/or disposable container for electronic vaporizer device 100. For example, cartridge 302 may contain a predetermined amount of a vaporizable substance and when the vaporizable substance is used up or near to be used up, a user of electronic vaporizer device 100 may remove cartridge 302 from electronic vaporizer device 100 and install another cartridge 302. In some non-limiting embodiments, the vaporizable substance may be any composition, material, or matter that produces a vapor for inhalation by a human being when heated to a predetermined temperature. In some non-limiting embodiments, cartridge 302 may include an identifier that includes content information regarding the contents of cartridge 302. For example, the identifier may be incorporated into cartridge 302, e.g., as a barcode or other mechanism that may provide a signal regarding a vaporizable substance and/or susceptor element 304 within cartridge 302. In some non-limiting embodiments, the processor may be coupled to induction heating element 121 and/or programmed to read the content information of cartridge 302 so that it is used to set parameters and cause induction heating element 121 to apply a heating profile to the vaporizable substance according to the content information of cartridge 302. In some non-limiting embodiments, cartridge 302 may be a replaceable and/or disposable container for electronic vaporizer device 100. For example, cartridge 302 may contain a predetermined amount of a vaporizable substance, and when the vaporizable substance is used up or near to be used up, a user may replace cartridge 302 (e.g., with another cartridge).

In some non-limiting embodiments, vaporizer device 100 may include an indicator of the amount of vaporizable substance remaining in cartridge 302. For example, the indicator may be located on cartridge 302, on upper housing 109a, and/or on lower housing 109b of electronic vaporizer device 100. In some non-limiting embodiments, the indicator may include a digital or analog output screen located on electronic vaporizer device 100 that is visible to a user. In some non-limiting embodiments, electronic vaporizer device 100 may have a second indicator that indicates when cartridge 302 is close to empty and acts as a low volume indicator for the vaporizable substance.

In some non-limiting embodiments, cartridge 302 may be configured to be refilled with a vaporizable substance. Additionally or alternatively, cartridge 302 may be configured to be refilled while located within electronic vaporizer device 100 such as through a vent or aperture in housing 109a and/or lower housing 109b. In some non-limiting embodiments, induction heating element 121 and cartridge 302 may be formed as part of a replaceable assembly such that cartridge assembly 300 (e.g., cartridge 302, susceptor element 304 located within cartridge 302), induction heating element 121, and heating element body 123 may form the replaceable assembly and may be removed from electronic vaporizer device 100 and replaced as a unitary component. In one example, such a replaceable assembly may include electrical connections to connect induction heating element 121 to electronic control components 101.

In some non-limiting embodiments, replacement of cartridge 302 may be accomplished by removing upper housing 109a and lower housing 109b and separating any additional components as necessary. In some non-limiting embodiments, replacement of cartridge 302 may be accomplished without removal of upper housing 109a and lower housing 109b. For example, electronic vaporizer device 100 may allow a user to remove cartridge 302 that is empty (e.g., a cartridge in which a vaporizable substance has been depleted) and to replace cartridge 302 with another cartridge 302 that includes an amount of a vaporizable substance within induction heating element 121 without removing any components. In some non-limiting embodiments, vaporizer device 100 may include a channel or chamber that allows for removal of cartridge 302 and allows for replacement of cartridge 302. In some non-limiting embodiments, electronic vaporizer device 100 may include a chamber or channel that may be manipulated (e.g., folded, twisted, and/or the like) to open to accept a new cartridge 302 and then may be manipulated to close and place cartridge 302 in the appropriate position (e.g., to enable heating of the vaporizable substance within cartridge 302). In some non-limiting embodiments, upper housing 109a and lower housing 109b may have a chamber or channel defined therein, and upper housing 109a and lower housing 109b may be configured to receive cartridge 302 within the chamber or channel.

In some non-limiting embodiments, power may be provided to induction heating element 121 and/or electronic control components 101 from power source 111. In some non-limiting embodiments, power source 111 may be sized appropriately for an application (e.g., placement within electronic vaporizer device 100). In some non-limiting embodiments, power source 111 may include an alternating current (AC) power supply (e.g., a generator, an alternator, etc.) and/or a direct current (DC) power supply (e.g., a battery, a capacitor, a fuel cell, etc.). In some non-limiting embodiments, power source 111 may be any form of a device that includes one or more electrochemical cells that convert stored chemical energy into electrical energy. For example, power source 111 may be a battery. The battery may be a primary battery, a secondary battery, a rechargeable battery, and/or the like. Additionally or alternatively, the battery may include an alkaline battery, a watch battery, a Lithium Ion battery, and/or the like.

In some non-limiting embodiments, induction heating element 121 may be inductively coupled to susceptor element 304 within the cartridge 302. For example, induction heating element 121 may be inductively coupled to susceptor element 304 located within cartridge 302 and not in contact with susceptor element 304. Susceptor element 304 may be heated by electromagnetic induction, through heat generated in susceptor element 304 by eddy currents flowing in susceptor element 304. In some non-limiting embodiments, susceptor element 304 may be configured to heat substances that are adjacent to and/or in contact with the material of susceptor element 304. For example, a vaporizable substance may be heated based on induction heating of susceptor element 304 by induction heating element 121. In some non-limiting embodiments, susceptor element 304 may be configured to transfer a vaporizable substance from a reservoir of cartridge 302 based on a capillary action of susceptor element 304.

In some non-limiting embodiments, electronic control components 101 of electronic vaporizer device 100 may include a circuit that includes a current generating device, a processor, and at least one sensor. Additionally or alternatively, the power supplied to induction heating element 121 may be controlled by the processor, which may provide precise monitoring and/or control of the power supplied to induction heating element 121 on a time scale that may be as low as a few milliseconds. In some non-limiting embodiments, the processor may be configured to receive information from the sensor and/or able to adjust a heating profile applied to susceptor element 304 by induction heating element 121. In some non-limiting embodiments, the sensor may be able to detect and/or calculate information, such as airflow from or into electronic vaporizer device 100, pressure at locations within electronic vaporizer device 100 or of the vapor exiting electronic vaporizer device 100, temperature of the components or locations near the components of electronic vaporizer device 100, such as the temperature of induction heating element, and/or the like. In some non-limiting embodiments, such features may allow the circuit to sense that a user of electronic vaporizer device 100 is beginning to inhale and/or that a power level may be increased to compensate for a tendency of the incoming air to cool susceptor element 304 (e.g., below susceptor element's 304 ideal temperature, operating temperature range, and/or the like). In some non-limiting embodiments, when an active inhalation is not in progress, the circuit may be able to then reduce the power, which may improve the life of power source 111.

In some non-limiting embodiments, the processor may be able to use the information to calculate and/or implement a temperature profile (e.g., optimal temperature profile and/or the like). Additionally or alternatively, the processor may be configured to adjust a heating profile applied to susceptor element 304 by induction heating element 121 based on the vaporizable substance. For example, the processor may be able to implement a predetermined heating profile according to a vaporizable substance (e.g., a vaporizable substance located in cartridge 302). In some non-limiting embodiments, the processor may allow the user to modify the settings and/or the entire algorithm for providing the heat in order to obtain an improved experience (e.g., preferred experience, best experience, and/or the like). In some non-limiting embodiments, the design and/or configuration of all of electronic control components 101 may be sufficiently energy efficient to allow electronic vaporizer device 100 to be hand held and battery operated. Additionally or alternatively, the electronic components may include a printed circuit board and, in some non-limiting embodiments, the processor may include a microprocessor, a microcontroller, and/or the like.

Figure 2:
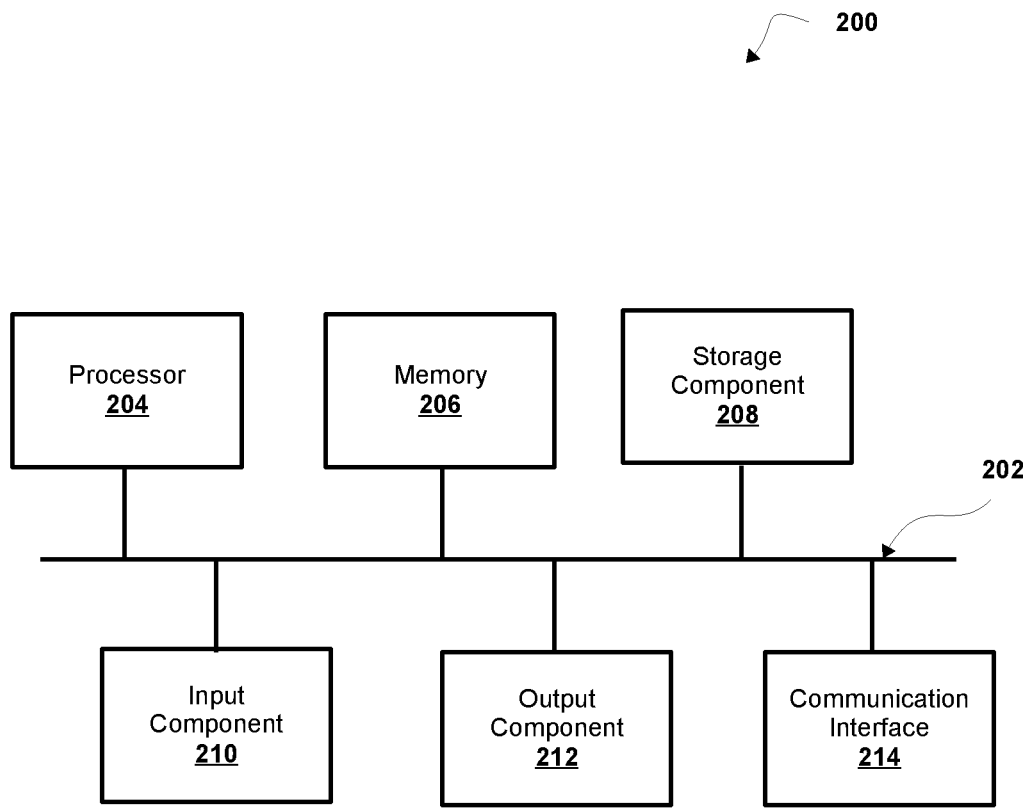
FIG. 2 is a diagram of a non-limiting embodiment of components of an electronic vaporizer device according to the present disclosure.

Referring now to FIG. 2, FIG. 2 is a diagram of example components of a device 200. Device 200 may correspond to electronic control components 101. In some non-limiting embodiments, electronic control components 101 may include at least one device 200 and/or at least one component of device 200. As shown in FIG. 2, device 200 may include bus 202, processor 204, memory 206, storage component 208, input component 210, output component 212, and communication interface 214.

Bus 202 may include a component that permits communication among the components of device 200. In some non-limiting embodiments, processor 204 may be implemented in hardware, software, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read-only memory (ROM), and/or another type of dynamic or static storage device (e.g., flash memory, magnetic memory, optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally or alternatively, input component 210 may include a sensor for sensing information (e.g., a temperature sensor, an accelerometer, a gyroscope, an actuator, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmitter, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally or alternatively, hardwired circuitry may be used in place of or in combination with software instructions to perform one or more processes described herein. Thus, embodiments described herein are not limited to any specific combination of hardware circuitry and software.

The number and arrangement of components shown in FIG. 2 are provided as an example. In some non-limiting embodiments, device 200 may include additional components, fewer components, different components, or differently arranged components than those shown in FIG. 2. Additionally or alternatively, a set of components (e.g., one or more components) of device 200 may perform one or more functions described as being performed by another set of components of device 200.

Figure 3:
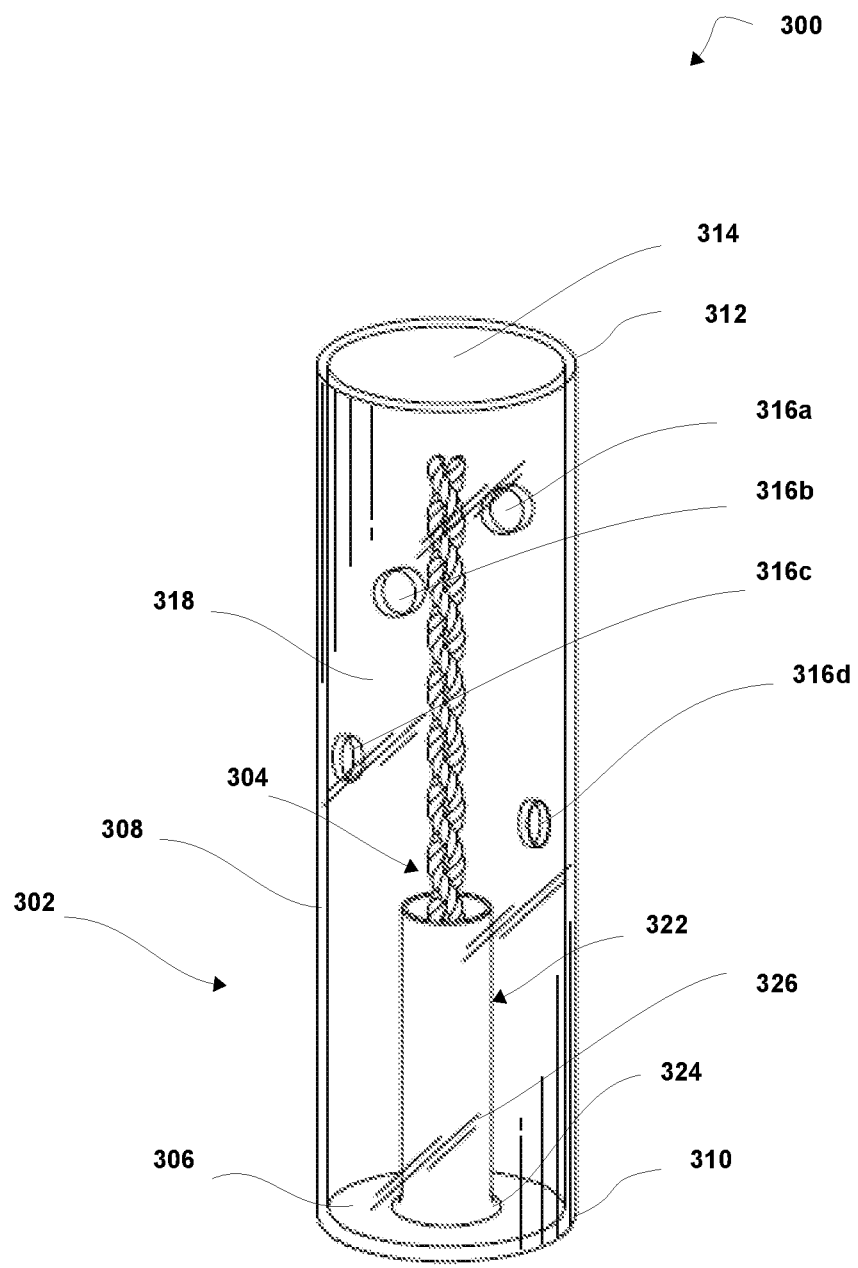
FIG. 3 is a diagram of a non-limiting embodiment of a cartridge assembly according to the present disclosure.

Referring now to FIG. 3, FIG. 3 is a diagram of a cartridge assembly 300. As shown in FIG. 3, cartridge assembly 300 may include cartridge 302 and susceptor element 304. In some non-limiting embodiments, cartridge 302 may include base section 306 and one or more side sections 308. For example, as shown in FIG. 3, cartridge 302 may have a cylindrical shape (e.g., a shape corresponding to a right circular cylinder) and cartridge 302 may include side section 308. In another example, cartridge 302 may have a rectangular prism shape and cartridge 302 may include a plurality of side sections 308. In some non-limiting embodiments, cartridge 302 may have a shape that is sized appropriately for an application. For example, cartridge 302 may have a shape that allows cartridge 302 to fit within induction heating element 121. In some non-limiting embodiments, cartridge 302 may have a length in the range of 20 mm to 40 mm. In one example, cartridge 302 may have a length of 32 mm. In some non-limiting embodiments, cartridge 302 may have an outer diameter (e.g., a distance between one or more side sections 308) in the range of 8 mm to 20 mm. For example, cartridge 302 may have an outer diameter equal to 10 mm. In some non-limiting embodiments, side section 308 of cartridge 302 may have a width in the range of 0.5 mm to 2 mm. For example, side section 308 of cartridge 302 may have a width of 1 mm. In some non-limiting embodiments, an inner diameter of cartridge 302 may be in the range of 5 mm to 15 mm. For example, the inner diameter of cartridge 302 may be 8 mm. In some non-limiting embodiments, cartridge 302 may be made of an appropriate material (e.g., an insulating material) such as glass, fiberglass, plastic, ceramic, and/or the like. In some non-limiting embodiments, cartridge 302 may be made of a material that is transparent, such as glass, so that the contents of the interior chamber of cartridge 302 may be viewed by a user.

As further shown in FIG. 3, side section 308 may be coupled to base section 306 at first end 310 of side section 308, wherein aperture 314 is defined at second end 312 of side section 308. Side section 308 may include one or more apertures. As shown in FIG. 3, side section 308 may include apertures 316a-d located in side section 308, where apertures 316a-d are configured to allow air to flow into interior chamber 318 of cartridge 302 when air flows out of aperture 314 defined at second end 312. In some non-limiting embodiments, apertures 316a-d are configured to allow a volume of air into interior chamber 318 of cartridge 302, wherein the volume of air may be based on a volume per unit of length of cartridge 302. For example, the volume of air may be proportional to a volume of cartridge 302 that is calculated based on a specified unit of length of cartridge 302. In some non-limiting embodiments, apertures 316a-d may have a shape that is appropriate for an application. For example, apertures 316a-d may have a circular shape, an oval shape, and/or the like. In some non-limiting embodiments, an aperture (e.g., one or more of apertures 316a-d) may have a diameter in the range of 0.5 mm to 2 mm. For example, the aperture may have a diameter equal to 1 mm. In some non-limiting embodiments, a first aperture in side section 308 may be larger or smaller (e.g., larger or smaller with respect to an amount of air flow through the aperture) than a second aperture in side section 308. For example, the first aperture in side section 308 may have a diameter that is larger or smaller than a diameter of the second aperture in side section 308.

As further shown in FIG. 3, susceptor element 304 may be located within cartridge 302 and susceptor element 304 may include susceptor element 304 and shielding element 322. In some non-limiting embodiments, susceptor element 304 may be the same or similar to a susceptor described above. In some non-limiting embodiments, the materials used in susceptor element 304 may include a ferromagnetic material and/or a metallic conductor. Additionally or alternatively, susceptor element 304 may include materials that produce heat eddy currents and/or magnetic hysteresis when susceptor element 304 is exposed to an electromagnetic field. For example, ferromagnetic materials and/or metallic conductor materials that have considerable hysteresis in the range of electromagnetic fields may be used to construct susceptor element 304. In some non-limiting embodiments, susceptor element 304 may include a material such that heating is carried out both by eddy currents and also by movement of the magnetic domain walls. In some non-limiting embodiments, susceptor element 304 may be made of a material capable of absorbing electromagnetic energy, generating heat based on electromagnetic energy that is absorbed, and/or providing heat (e.g., providing heat via conduction, providing heat via radiation, etc.) to an object (e.g., a substance, a device, a component, etc.) that is in thermal contact with susceptor element 304. For example, susceptor element 304 may include a material that is electrically conductive. In some non-limiting embodiments, susceptor element 304 may include a metallic conductor that heats by eddy currents. In some non-limiting embodiments, susceptor element 304 may be made from iron, steel (e.g., stainless steel, non-magnetic stainless steel, magnetic stainless steel, etc.), a ceramic magnet (e.g., ferrite), an FeCrAl alloy (e.g., Kanthal®), a semiconductor, and/or a combination thereof.

In one example, susceptor element 304 may be made from 304V stainless steel alloy and/or 430 stainless steel alloy.

In some non-limiting embodiments, susceptor element 304 may include a plurality of wire strands that are wound (e.g., twisted) together. For example, susceptor element 304 may include two, three, four, or more wire strands that are wound together in a helical formation. In some non-limiting embodiments, susceptor element 304 may include a first wire segment that includes a plurality of wire strands that are wound together in a helical formation and a second wire segment that includes a plurality of wire strands that are wound together in a helical formation. The first wire segment and the second wire segment may be wound together in a helical formation.

In some non-limiting embodiments, one or more wire strands may include a ferromagnetic material or a non-ferromagnetic material. For example, a wire strand may include steel (e.g., stainless steel) or aluminum. In some non-limiting embodiments, a diameter of a wire strand may be in the range of 0.25 mm to 1.5 mm (e.g., #30 American Wire Gauge (AWG) to % 15 AWG). For example, a diameter of a wire strand may be 1 mm. In some non-limiting embodiments, one or more wire strands may include a coating. For example, one or more wire strands may include a coating of a ceramic material and/or a glass material, such as zirconia, silicon dioxide, alumina, and/or the like. In some non-limiting embodiments, a thickness of the coating may be in the range of 0.1 mm to 0.3 mm. For example, the thickness of the coating may be 0.15 mm or 0.25 mm.

In some non-limiting embodiments, susceptor element 304 may have a length such that susceptor element 304 fits entirely within (e.g., no portion of susceptor element 304 extends out of) cartridge 302. In some non-limiting embodiments, susceptor element 304 may have a length in the range of 10 mm to 35 mm. In one example, the susceptor element may have a length of 32 mm.

In some non-limiting embodiments, susceptor element 304 may include a plurality of wire strands that are wound together and the susceptor element 304 may have a pitch based on the diameter of a wire strand of the plurality of wire strands. As described herein, pitch refers to a length of susceptor element 304 in terms of a diameter of a wire (e.g., a wire strand, a plurality of wire strands, etc.) that corresponds to one complete turn (e.g., 360 degrees) of a wire that makes up susceptor element 304. For example, susceptor element 304 may include a plurality of wire strands, each having the same diameter, that are wound together and the susceptor element 304 may have a pitch in the range of 25 wire diameters to 1 wire diameter. As the formula for the pitch is a length of one complete turn of wire divided by a diameter of the wire, a value for the pitch is given as a number of wire diameters. In one example, susceptor element 304 may operate at a frequency in the range of 50 kHz to 150 kHz (e.g., 100 kHz), and susceptor element 304 may include two #26 AWG wire strands of FeCrAl alloy wound together in a helical formation and having a pitch of 9.4 wire diameters. The two wire strands may be wound together in a helical formation with sixteen, #48 AWG, wire strands made from 304V stainless steel alloy. In another example, susceptor element 304 may operate at a frequency in the range of 50 kHz to 150 kHz (e.g., 100 kHz), and susceptor element 304 may include four #28 AWG wire strands of FeCrAl alloy wound together in a helical formation and having a pitch of 11.9 wire diameters. The four wire strands may be wound together in a helical formation with sixteen #48 AWG wire strands made from 430 stainless steel alloy.

In some non-limiting embodiments, susceptor element 304 may have a configuration that includes a stranded wire, a stranded rope of material, a mesh, a mesh tube, several concentric mesh tubes, a cloth, a sheet of material, a porous solid (e.g., a foam), a roll of metal mesh, fibers of metal, or any other geometry that is appropriately sized and configured. In some non-limiting embodiments, susceptor element 304 may include fins, protrusions, or other details that are configured to hold a solid and/or a semi-solid material in thermal contact with susceptor element 304.

In some non-limiting embodiments, susceptor element 304 may be constructed of a combination of materials to achieve an appropriate effect. For example, susceptor element 304 may be an interwoven cloth (or otherwise intimately mixed combination) of wires that are to be used for induction heating. Additionally or alternatively, the materials of susceptor element 304 may be combined with a rope or foam, or suitably deployed thin sheets of material. In some non-limiting embodiments, the susceptor element may include rolled up alternating foils of material. Additionally or alternatively, susceptor element 304 may be surrounded by induction heating element 121, which may not be in contact with the mesh. In some non-limiting embodiments, as the susceptor element may be formed from a mesh, the mesh wick may be made of a material that is efficiently heated by induction (e.g., a FeCrAl alloy). In some non-limiting embodiments, the mesh wick may be formed using a Kanthal mesh. Additionally or alternatively, susceptor element 304 and/or shielding element 322 may be removable from cartridge 302 so that susceptor element 304 and/or shielding element 322 may be able to be cleaned, reused, and/or replaced separate from cartridge 302.

As further shown in FIG. 3, shielding element 322 may include lower flange section 324 and body section 326. In some non-limiting embodiments, shielding element 322 may be located within cartridge 302 and susceptor element 304 may be located within shielding element 322. In some non-limiting embodiments, shielding element 322 may have a tubular shape. For example, body section 326 of shielding element 322 may have a tubular shape to allow for susceptor element to be located within an interior of shielding element 322. In some non-limiting embodiments, shielding element 322 surrounds a portion of susceptor element 304 when susceptor element 304 is located within shielding element 322. In this way, shielding element 322 may shield susceptor element 304 from electromagnetic radiation provided by induction heating element 121 when electronic vaporizer device 100 is in use. Additionally, shielding element 322 may reduce an amount of electromagnetic radiation absorbed by susceptor element 304 to prevent degradation of a vaporizable substance that is adjacent to or in contact with shielding element 322.

In some non-limiting embodiments, lower flange section 324 may be sized and configured to contact base section 306 of cartridge 302 and to allow shielding element 322 to stand upright within cartridge 302. For example, lower flange section 324 may contact base section 306 and be positioned within a reservoir of cartridge 302. In some non-limiting embodiments, lower flange section 324 may be sized and configured to control an amount of the vaporizable substance that moves into an interior of shielding element 322 from a reservoir of cartridge 302 after an amount of the vaporizable substance is vaporized by susceptor element 304. In some non-limiting embodiments, shielding element 322 may be sized and configured to hold a predetermined amount of a vaporizable substance adjacent to or in contact with susceptor element 304. In some non-limiting embodiments, shielding element 322 may have a diameter in the range of 2 mm to 5 mm. For example, shielding element 322 may have a diameter equal to 3 mm. In some non-limiting embodiments, lower flange section 324 may have an outer diameter in the range of 3 mm to 7 mm. For example, lower flange section 324 may have an outer diameter equal to 5 mm. In some non-limiting embodiments, shielding element 322 may include an upper flange section (as described below).

In some non-limiting embodiments, shielding element 322 may be made from a material that does not react to an electromagnetic field. For example, shielding element 322 may be made from glass, fiberglass, plastic, and/or the like. In some non-limiting embodiments, shielding element 322 may be made from a metallic conductor, such as steel (e.g., stainless steel), aluminum, and/or the like. In some non-limiting embodiments, susceptor element 304 may include a first ferromagnetic material and shielding element 322 may include a second ferromagnetic material, and the first ferromagnetic material has greater ferromagnetic properties (e.g., responds more strongly to a magnetic field or an electromagnetic field) than the second ferromagnetic material.

In some non-limiting embodiments, cartridge 302 may include a reservoir within interior chamber 318 to hold a vaporizable substance. For example, base section 306 and side section 308 may define a fluid reservoir. In some non-limiting embodiments, susceptor element 304 may be configured to be located within the reservoir and susceptor element 304 may contact the vaporizable substance of the reservoir. In some non-limiting embodiments, susceptor element 304 is configured to heat the vaporizable substances that are adjacent or in contact with susceptor element 304. For example, a vaporizable substance may be heated based on induction heating of susceptor element 304 by induction heating element 121. According to embodiments, susceptor element 304 may also be configured to transfer a vaporizable substance from a reservoir of cartridge 302 based on a capillary action of susceptor element 304. In embodiments where the vaporizable substance includes a viscous substance (e.g., a liquid), as an amount of the viscous substance is vaporized based on heating by susceptor element 304, another amount of the viscous substance may move up susceptor element 304 based on a capillary action of susceptor element 304.

In some non-limiting embodiments, susceptor element 304 may be located within cartridge 302, and susceptor element 304 may be heated via induction without electrical connections to a power source (e.g., power source 111). Additionally or alternatively, cartridge 302 may have an interior surface, and susceptor element 304 may be positioned adjacent to or in contact with the interior surface of cartridge 302. Additionally or alternatively, a portion of cartridge 302 may act as an insulating member between susceptor element 304 and the induction heating element 121. For example, such an insulating member may remove (e.g., separate) the induction heating element 121 from contact with the vaporizable substance (e.g., a liquid) in cartridge 302.

Figure 4A:
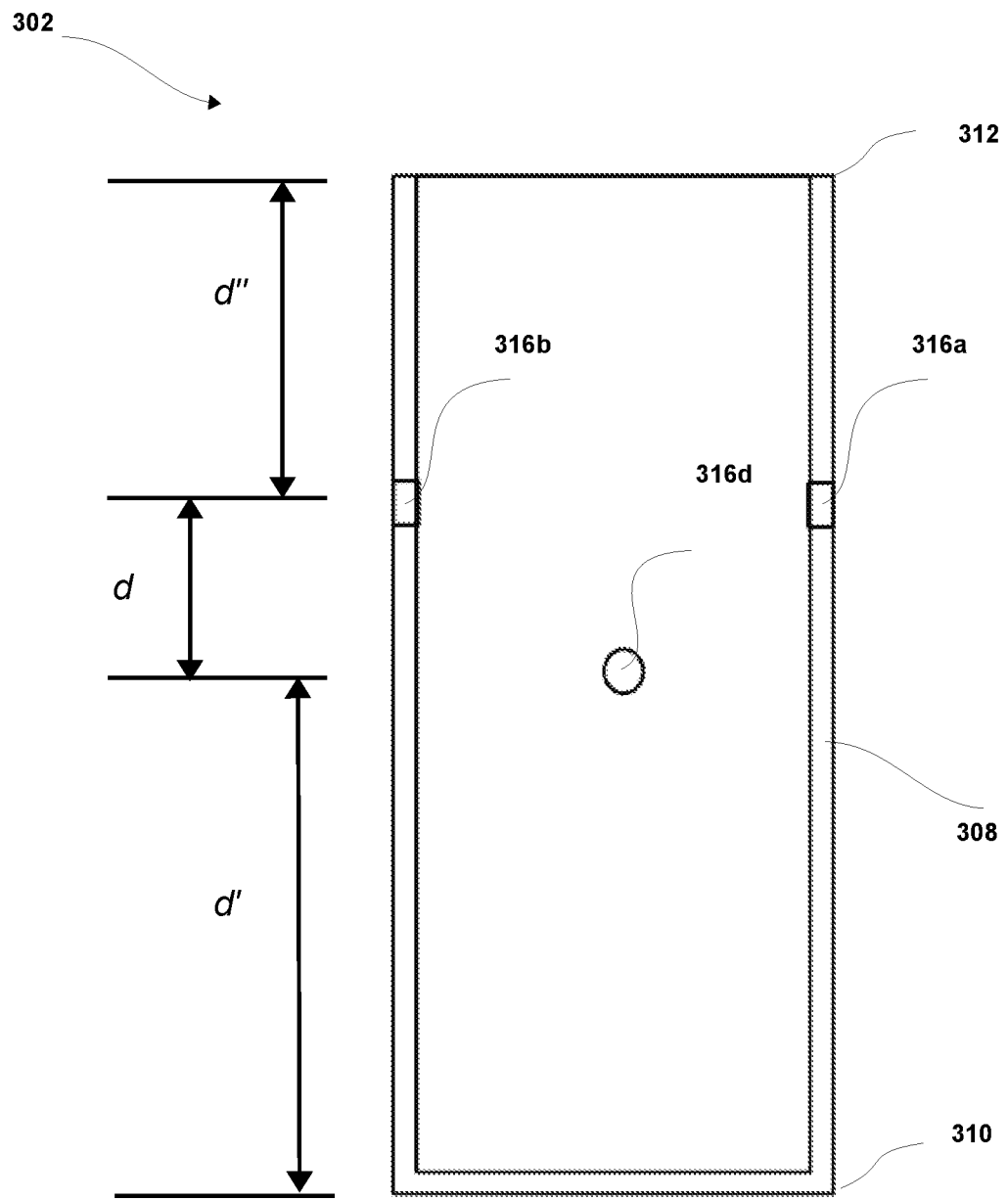
FIGS. 4a and 4b are diagrams of a non-limiting embodiment of a cartridge according to the present disclosure.
Figure 4B:
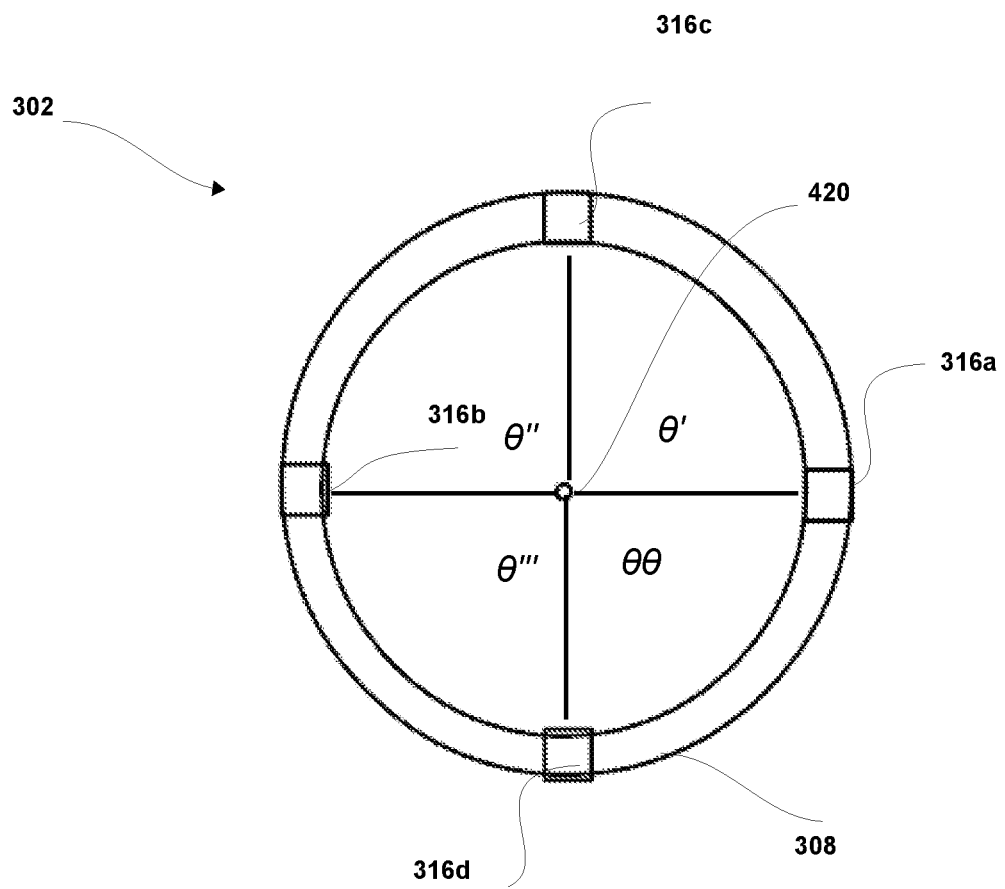

Referring now to FIGS. 4a and 4b, FIGS. 4a and 4b are diagrams of cartridge 302 and provide details regarding the apertures in side section 308 of cartridge 302. FIG. 4a is a front view of cartridge 302 and FIG. 4b is top down view of cartridge 302. As shown in FIGS. 4a and 4b, apertures 316a and 316b are adjacent second end 312 of side section 308 and apertures 316d and 316c are adjacent apertures 316a and 316b. It is noted that 316c is not visible in FIG. 4a as aperture 316c is located opposite (e.g., behind) aperture 316d. As further shown in FIG. 4a, apertures 316a and 316b may be vertically offset from apertures 316d and 316c by a distance, d. In some non-limiting embodiments, distance d may have a value in the range of 2 mm to 8 mm. For example, distance d may have a value equal to 3 mm. In some non-limiting embodiments, each of apertures 316a and 316b may be vertically offset from aperture 316d (e.g., or aperture 316c) by a distance that is the same or by a distance that is different. For example, aperture 316a may be vertically offset from aperture 316d by a first distance and aperture 316b may be vertically offset from aperture 316d by a second distance, where the first distance and the second distance are the same or different.

As further shown in FIG. 4a, apertures 316d and 316c may be vertically offset from first end 310 of cartridge 302 by distance d'. In some non-limiting embodiments, distance d' may have a value in the range of 15 mm to 25 mm. For example, distance d' may have a value equal to 20 mm. In some non-limiting embodiments, each of apertures 316d and 316c may be vertically offset from first end 310 by a distance that is the same or by a distance that is different. As further shown in FIG. 4a, apertures 316b and 316a may be vertically offset from second end 312 of cartridge 302 by distance d". In some non-limiting embodiments, distance d" may have a value in the range of 8 mm to 15 mm. For example, distance d" may have a value equal to 12 mm. In some non-limiting embodiments, each of apertures 316b and 316a may be vertically offset from first end 310 by a distance that is the same or by a distance that is different.

As further shown in FIG. 4b, apertures 316a, 316b, 316c, and 316d may be horizontally offset from an adjacent aperture. For example, as shown in FIG. 4b, aperture 316d may be horizontally offset from aperture 316a. In such an example, an angle θ is formed between a first line from center axis 420 (e.g., a longitudinal center axis) of cartridge 302 to aperture 316d and a second line from center axis 420 to aperture 316a. The angle θ may be a value that indicates an amount of horizontal offset between aperture 316d and aperture 316a based on a circumference of cartridge 302. As shown in FIG. 4b, each of apertures 316a, 316b, 316c, and 316d may be horizontally offset by 90 degrees from an adjacent aperture (e.g., each of θ, θ', θ", and θ'" may be equal to 90 degrees). In some non-limiting embodiments, each of apertures 316a, 316b, 316c, and 316d may be horizontally offset by a different angle (e.g., each of θ, θ', θ", and θ'" may be equal to a different value) from an adjacent aperture.

Figure 5:
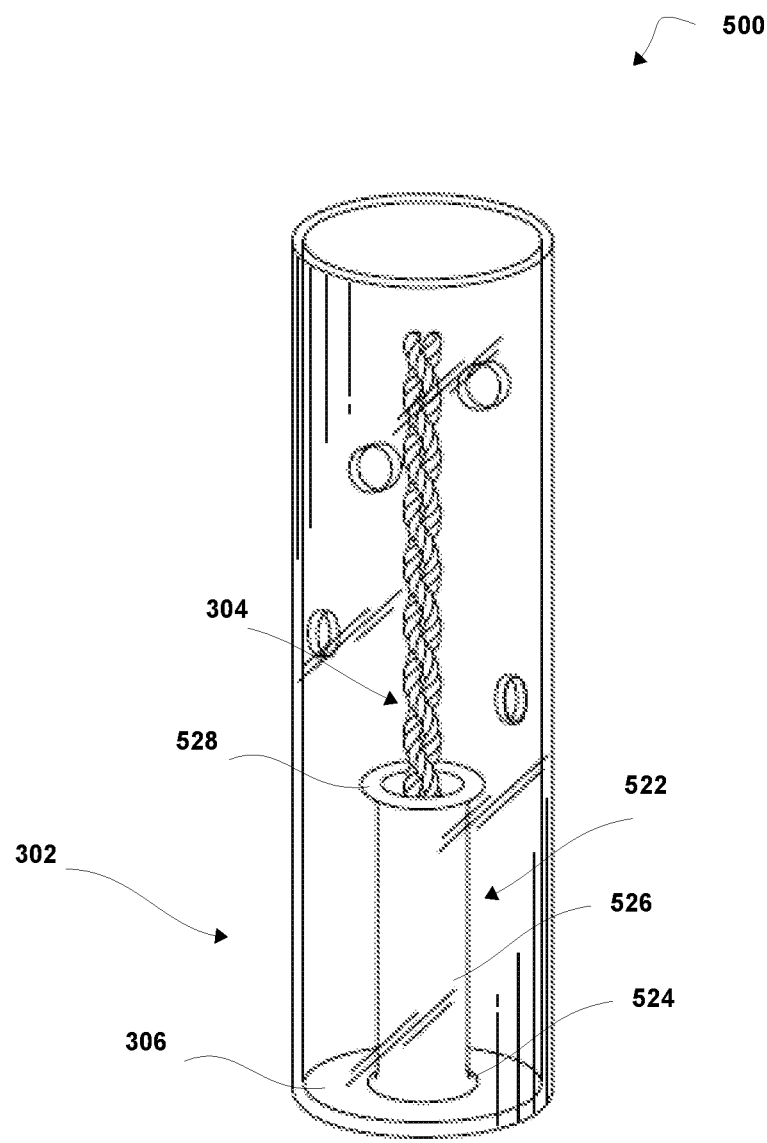
FIG. 5 is a diagram of a non-limiting embodiment of a cartridge assembly according to the present disclosure.

Referring now to FIG. 5, FIG. 5 is a diagram of cartridge assembly 500. In some non-limiting embodiments, cartridge assembly 500 may be the same or similar to cartridge assembly 300. Potential differences between cartridge assembly 500 and cartridge assembly 300 are indicated below. As shown in FIG. 5, cartridge assembly 500 may include cartridge 302, susceptor element 304, and shielding element 522. In some non-limiting embodiments, shielding element 522 may be the same or similar to shielding element 322. As shown in FIG. 5, shielding element 522 may include lower flange section 524, body section 526, and upper flange section 528. In some non-limiting embodiments, lower flange section 524 may be the same or similar to lower flange section 324. In some non-limiting embodiments, body section 526 may be the same or similar to body section 326.

In some non-limiting embodiments, upper flange section 528 may have a diameter that is the same as a diameter of lower flange section 524. In some non-limiting embodiments, upper flange section 528 may have a diameter that is larger than a diameter of lower flange section 524. In some non-limiting embodiments, upper flange section 528 may be sized and configured to contain a vaporizable substance located in a reservoir of cartridge 302, between upper flange section 528 and base section 306 of cartridge 302. For example, upper flange section 528 may be sized and configured to prevent a vaporizable substance located in a reservoir of cartridge 302 from moving (e.g., flowing, falling, etc.) past upper flange section 528 when shielding element 522 is located in cartridge 302.

Figure 6:
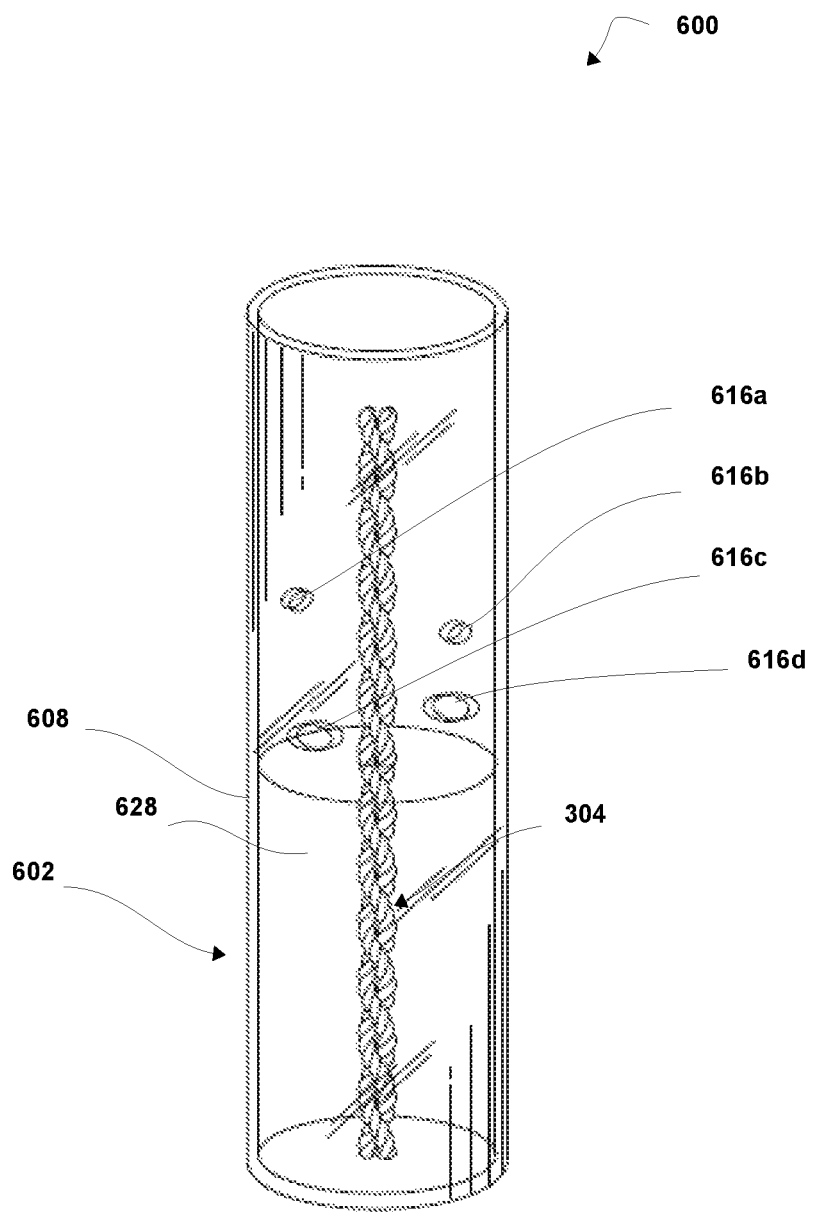
FIG. 6 is a diagram of a non-limiting embodiment of a cartridge assembly according to the present disclosure.

Referring now to FIG. 6, FIG. 6 is a diagram of cartridge assembly 600. In some non-limiting embodiments, cartridge assembly 600 may be the same or similar to cartridge assembly 300. Potential differences between cartridge assembly 600 and cartridge assembly 300 are indicated below. As shown in FIG. 6, cartridge assembly 600 may include cartridge 602 and susceptor element 304. In some non-limiting embodiments, cartridge 602 may be the same or similar to cartridge 302. Cartridge 602 may include a vaporizable substance 628 within cartridge 602 (e.g., within a reservoir of cartridge 602). As further shown in FIG. 6, cartridge 602 may include apertures 616a, 616b, 616c, and 616d in side section 608. Apertures 616a, 616b, 616c, and 616d may have an oval shape. Additionally, as further shown in FIG. 6, apertures 616c and 616d may be the same size and apertures 616a and 616b may be the same size, while apertures 616c and 616d are larger in size than apertures 616a and 616b.

Figure 7:
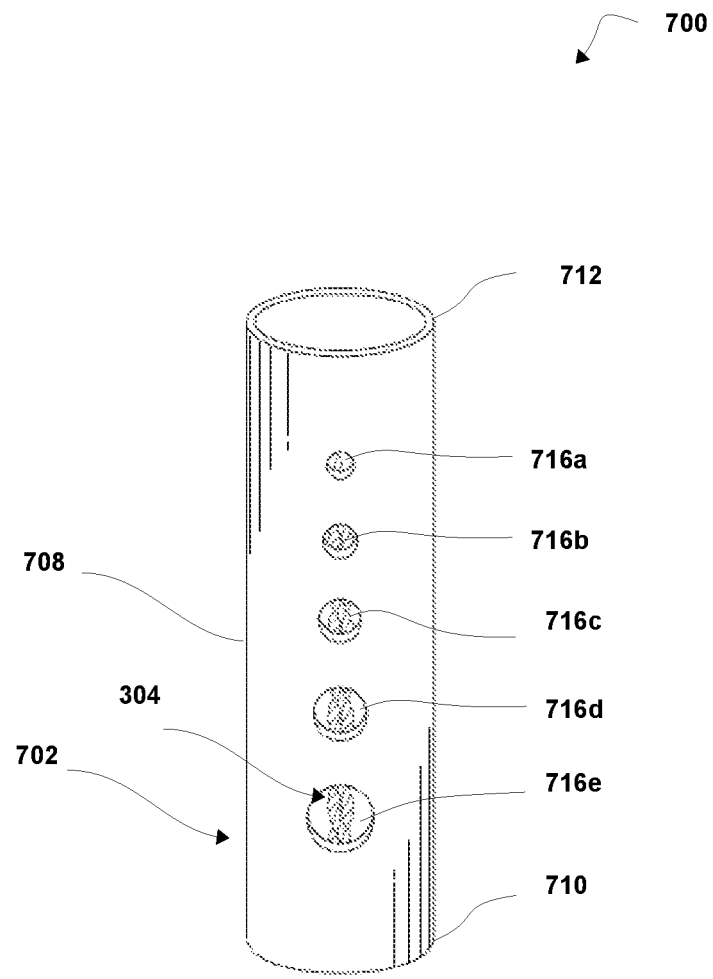
FIG. 7 is a diagram of a non-limiting embodiment of a cartridge assembly according to the present disclosure.

Referring now to FIG. 7, FIG. 7 is a diagram of cartridge assembly 700. In some non-limiting embodiments, cartridge assembly 700 may be the same or similar to cartridge assembly 300. Potential differences between cartridge assembly 700 and cartridge assembly 300 are indicated below. As shown in FIG. 7, cartridge assembly 700 may include cartridge 702 and susceptor element 304. In some non-limiting embodiments, cartridge 702 may be the same or similar to cartridge 302. Cartridge 702 may include a set of apertures, apertures 716a, 716b, 716c, 716d, and 716e in side section 708. As shown in FIG. 7, apertures 716a, 716b, 716c, 716d, and 716e may have a circular shape and may be vertically offset without being horizontally offset. Additionally, as further shown in FIG. 7, the set of apertures decrease in size moving from aperture 716e that is adjacent base section 710 to aperture 716a that is adjacent first end 712 of cartridge 702. In some non-limiting embodiments, another set of apertures (e.g., that are the same or similar to apertures 716a, 716b, 716c, 716d, and 716e), may be located in side section 708, horizontally offset from the set of apertures that includes apertures 716a, 716b, 716c, 716d, and 716e.

Figure 8:
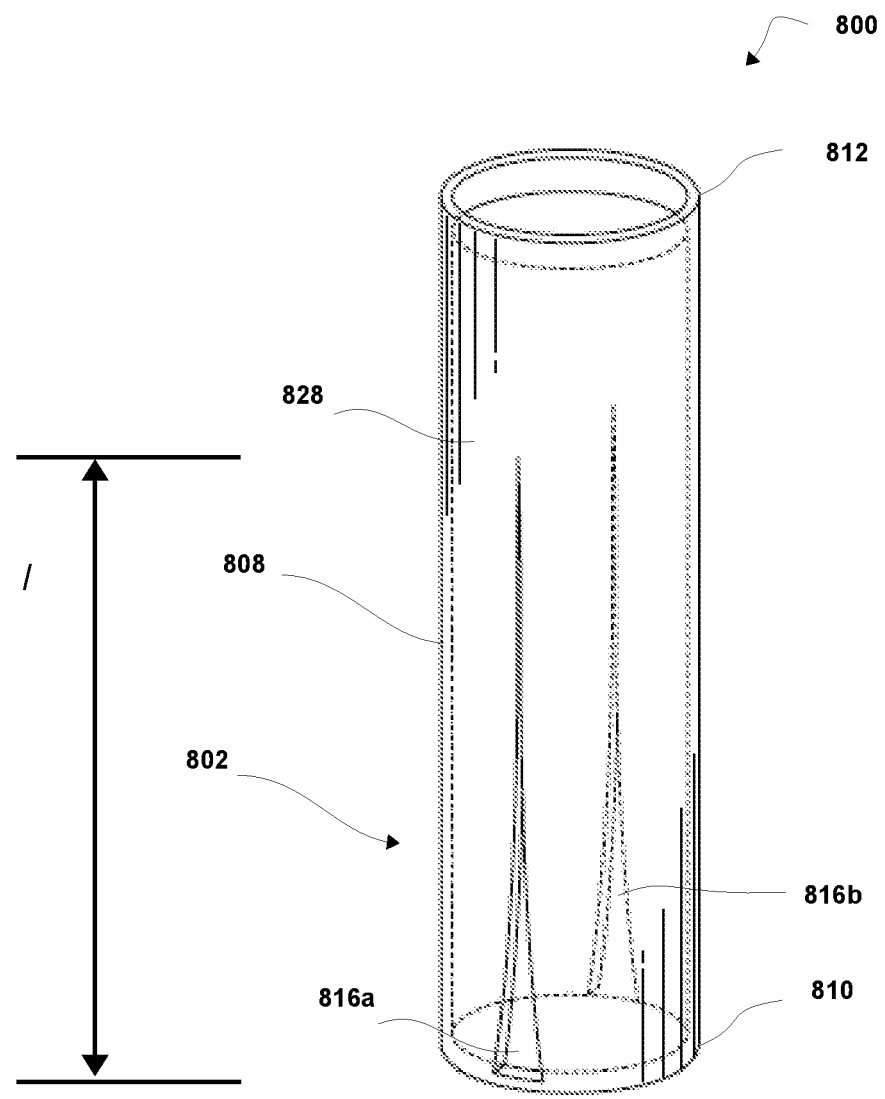
FIG. 8 is a diagram of a non-limiting embodiment of a cartridge assembly according to the present disclosure.

Referring now to FIG. 8, FIG. 8 is a diagram of cartridge assembly 800. In some non-limiting embodiments, cartridge assembly 800 may be the same or similar to cartridge assembly 300. Potential differences between cartridge assembly 800 and cartridge assembly 300 are indicated below. As shown in FIG. 8, cartridge assembly 800 may include cartridge 802 and, optionally, vaporizable substance 828. In some non-limiting embodiments, cartridge 802 may be the same or similar to cartridge 302. As further shown in FIG. 8, cartridge 802 may include slit apertures 816a and 816b located in side section 808 of cartridge 802. In some non-limiting embodiments, a size of an opening of each of slit apertures 816a and 816b may be greater at a location adjacent base section 810 of cartridge 802 than a size of the opening of slit apertures 816a and 816b adjacent second end 812 of side section 308. For example, the width of the opening of each of slit apertures 816a and 816b may taper from 1.5 mm at a location adjacent base section 810 to 0.1 mm adjacent second end 812 of side section 308. As further shown in FIG. 8, each of slit apertures 816a and 816b may have a length, l. In some non-limiting embodiments, l may have a value between 10 mm to 30 mm. For example, l may have a value equal to 28 mm.

Figure 9:
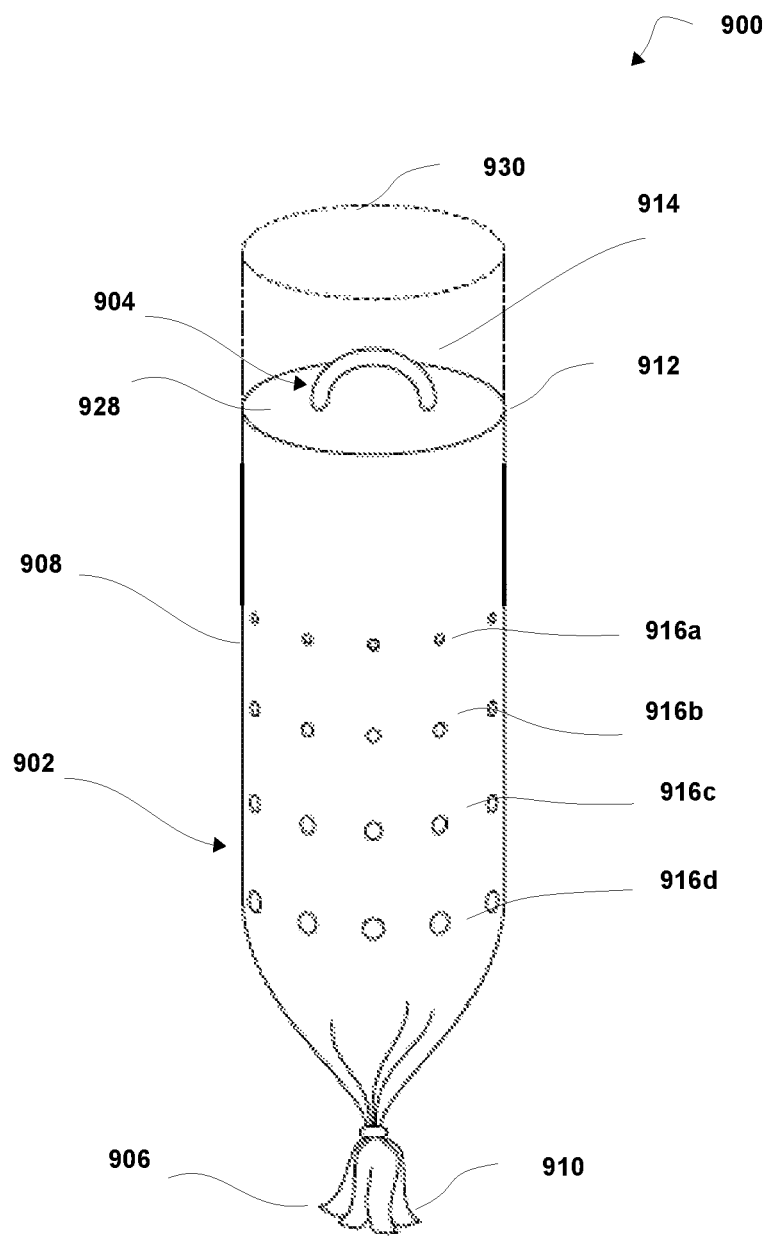
FIG. 9 is a diagram of a non-limiting embodiment of a cartridge assembly according to the present disclosure.

Referring now to FIG. 9, FIG. 9 is a diagram of cartridge assembly 900. In some non-limiting embodiments, cartridge assembly 900 may be the same or similar to cartridge assembly 300. Potential differences between cartridge assembly 900 and cartridge assembly 300 are indicated below. As shown in FIG. 9, cartridge assembly 900 may include cartridge 902, susceptor element 904, and, optionally, filter element 930. In some non-limiting embodiments, cartridge 902 may be the same or similar to cartridge 302. As further shown in FIG. 9, cartridge 902 may include side section 908 and base section 906. In some non-limiting embodiments, side section 908 may include first end 910 and second end 912, where an opening 914 is defined by second end 912. In some non-limiting embodiments, susceptor element 904 may be located within cartridge 902 and vaporizable substance 928 may be adjacent to and/or in contact with susceptor element 904. In some non-limiting embodiments, susceptor element 904 may be the same or similar to susceptor element 304. In some non-limiting embodiments, vaporizable substance 928 may include a non-viscous material, such as an herbal material (e.g., tobacco).

In some non-limiting embodiments, cartridge 902 may be formed from a material such as paper, a polymer, and/or herbal foil. In some non-limiting embodiments, base section 906 of cartridge may be formed based on crimping or twisting the material of cartridge 902 at first end 910 of side section 908 together. As further shown in FIG. 9, cartridge 902 may include a plurality of rows of apertures 916a, 916b, 916c, and 916d. The plurality of rows of apertures 916a, 916b, 916c, and 916d are configured to allow air to flow into an interior, which may include vaporizable substance 928, of cartridge 902 when air flows out of second end 912. In such an example, vaporizable substance 928 may be configured to allow air to flow through vaporizable substance 928 in the interior of cartridge 902. In some non-limiting embodiments, filter element 930 may be placed over second end 912 and filter element 930 may filter the air that flows out of second end 912. In some non-limiting embodiments, a size of the apertures in the plurality of rows of apertures 916a, 916b, 916c, and 916d decreases when viewed from the row of apertures 916d that is adjacent base section 906 to the row of apertures 916a that is adjacent second end 912.

Figure 10A:
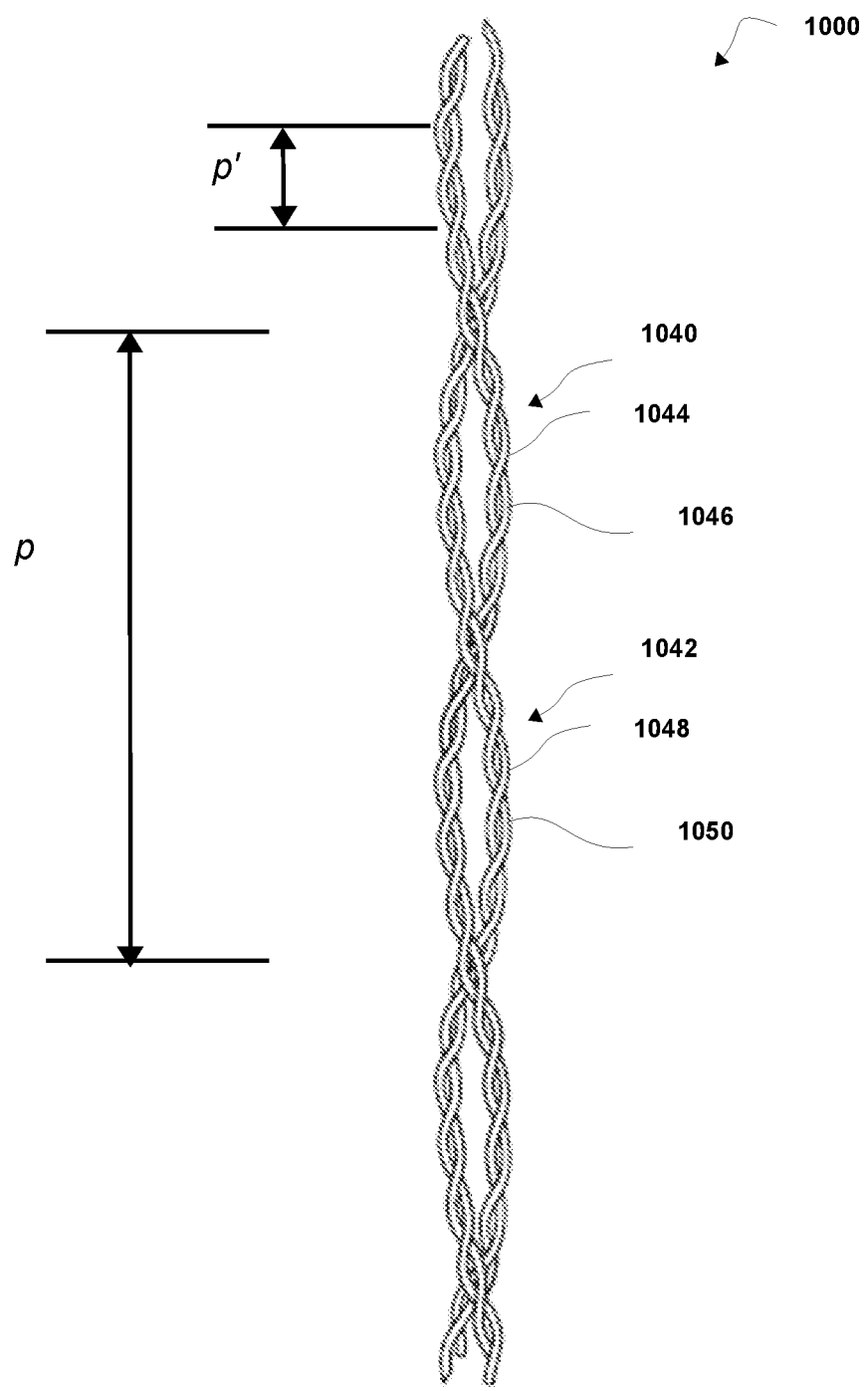
FIGS. 10a-10c are diagrams of a non-limiting embodiment of a susceptor element according to the present disclosure.

Referring now to FIG. 10a, FIG. 10a is a diagram of susceptor element 1000. In some non-limiting embodiments, susceptor element 304 may be the same or similar to susceptor element 1000, and vice versa. As shown in FIG. 10a, susceptor element 1000 may include first wire segment 1040 and second wire segment 1042. First wire segment 1040 may include first wire strand 1044 and second wire strand 1046. Second wire segment 1042 may include third wire strand 1048 and fourth wire strand 1050. As further shown in FIG. 10a, susceptor element 1000 may have a pitch, p, based on how first wire segment 1040 is wound with respect to second wire segment 1042. In the example shown in FIG. 10a, p may be equal to approximately 22 wire diameters based on the diameter of first wire segment 1040. In some non-limiting embodiments, the diameter of first wire segment 1040 may be equal to the diameter of second wire segment 1042. In some non-limiting embodiments, the diameter of first wire segment 1040 may not be equal to the diameter of second wire segment 1042.

As further shown in FIG. 10a, first wire segment 1040 may have a pitch, p', based on how first wire strand 1044 is wound with respect to and second wire strand 1046. In the example shown in FIG. 10a, p' may be equal to approximately 11 wire diameters based on the diameter of first wire strand 1044. In this example, the diameter of first wire strand 1044 is equal to the diameter of second wire strand 1046. In some non-limiting embodiments, the diameter of first wire strand 1044 may not be equal to the diameter of second wire strand 1046. In some non-limiting embodiments, one or more of first wire strand 1044, second wire strand 1046, third wire strand 1048, and fourth wire strand 1050 may be made of the same material. In some non-limiting embodiments, one or more of first wire strand 1044, second wire strand 1046, third wire strand 1048, and fourth wire strand 1050 may be made of a different material.

Figure 10B:
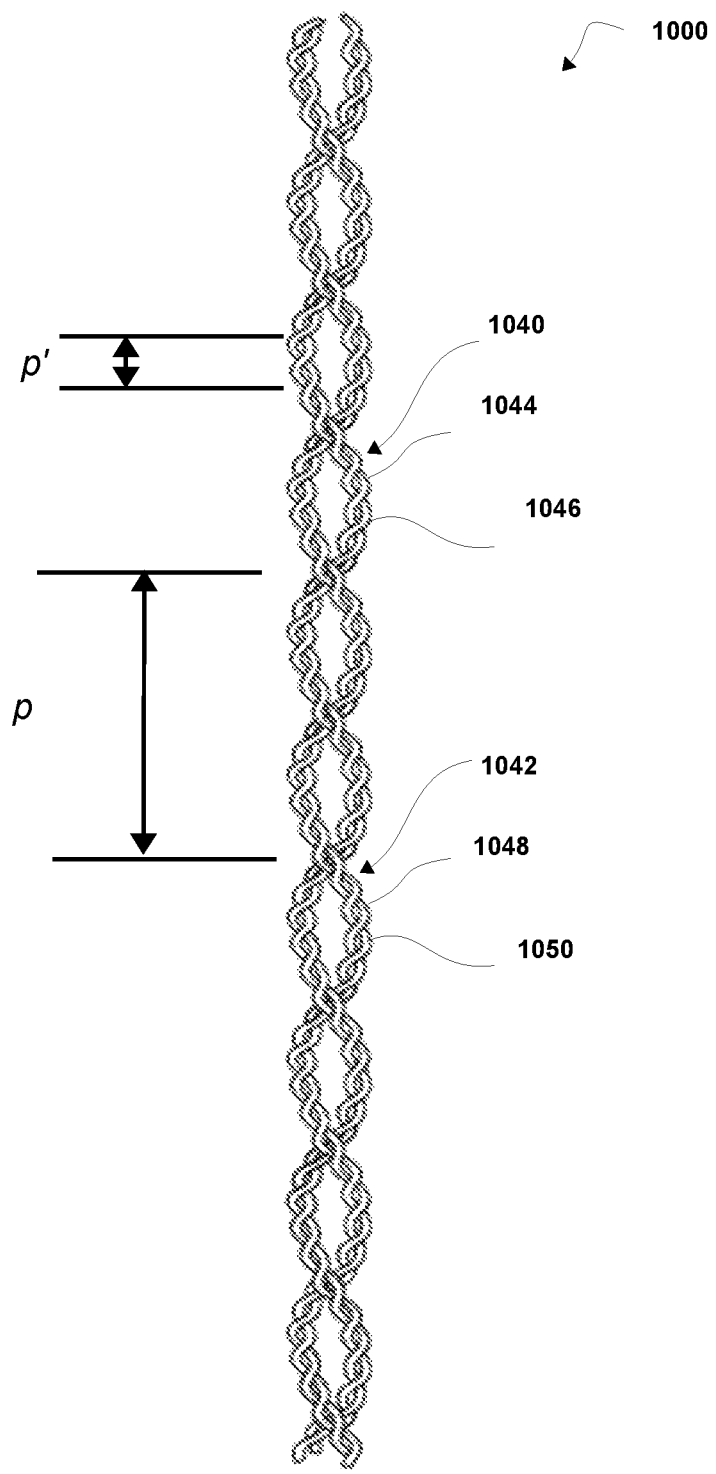

Referring now to FIG. 10b, FIG. 10b is another diagram of susceptor element 1000. As shown in FIG. 10b, the pitch, p, of susceptor element 1000 may decrease as compared to FIG. 10a based on how first wire segment 1040 is wound with respect to second wire segment 1042. In the example shown in FIG. 10b, p may be equal to approximately 11 wire diameters based on the diameter of first wire segment 1040. As further shown in FIG. 10b, the pitch, p', of first wire segment 1040 may decrease as compared to FIG. 10a based on how first wire strand 1044 is wound with respect to and second wire strand 1046. In the example shown in FIG. 10b, p' may be equal to approximately 5 wire diameters based on the diameter of first wire strand 1044.

Figure 10C:
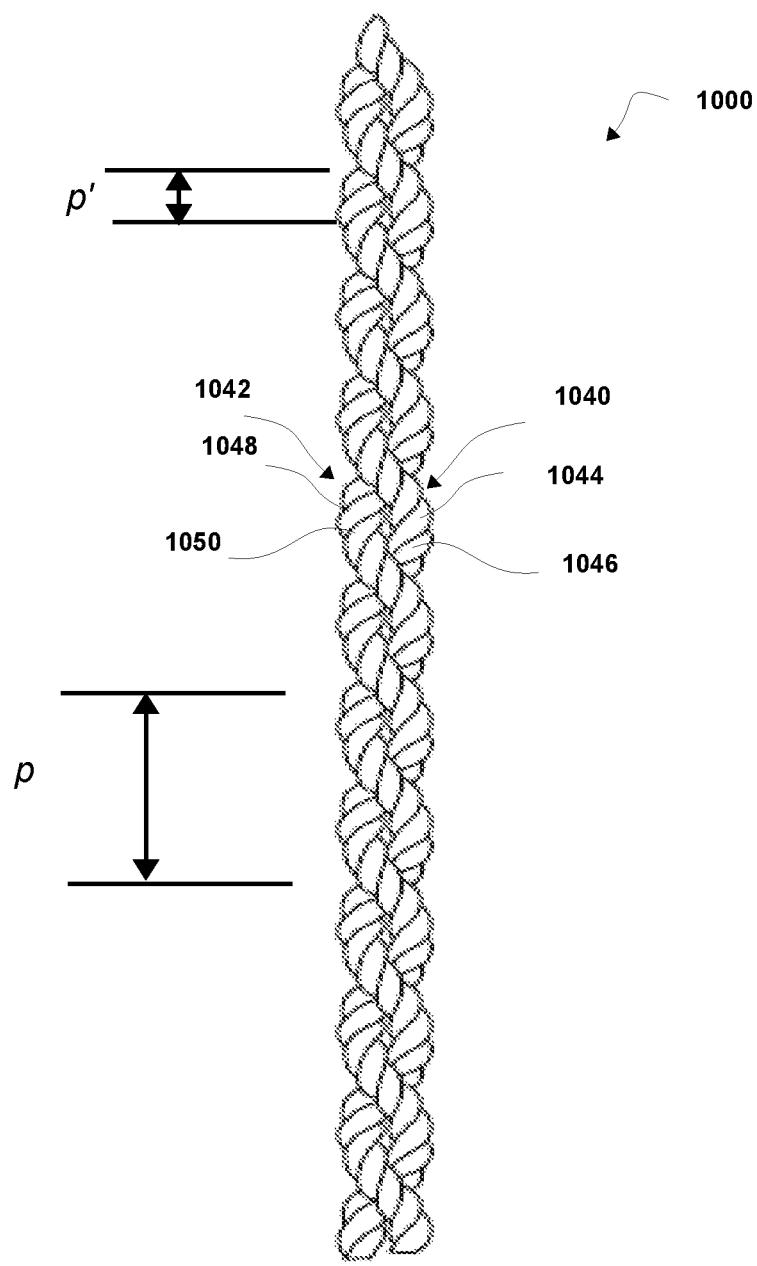

Referring now to FIG. 10c, FIG. 10c is another diagram of susceptor element 1000. As shown in FIG. 10c, the pitch, p, of susceptor element 1000 may decrease as compared to FIGS. 10a and 10b based on how first wire segment 1040 is wound with respect to second wire segment 1042. In the example shown in FIG. 10b, p may be equal to approximately 5 wire diameters based on the diameter of first wire segment 1040. As further shown in FIG. 10c, the pitch, p', of first wire segment 1040 may decrease as compared to FIGS. 10a and 10b based on how first wire strand 1044 is wound with respect to and second wire strand 1046. In the example shown in FIG. 10c, p' may be equal to approximately 2 wire diameters based on the diameter of first wire strand 1044.

Figure 11:
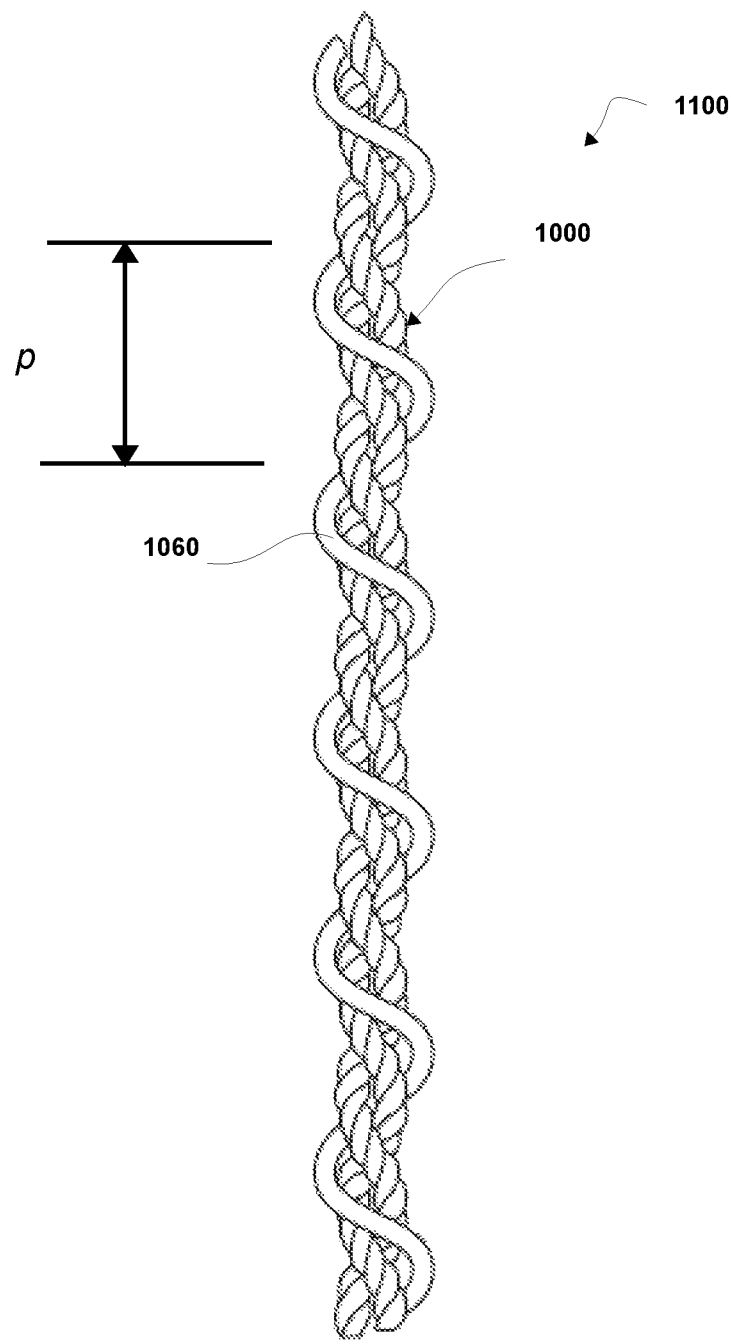
FIG. 11 is a diagram of a non-limiting embodiment of a susceptor element according to the present disclosure.

Referring now to FIG. 11, FIG. 11 is a diagram of susceptor element 1100. In some non-limiting embodiments, susceptor element 304 may be the same or similar to susceptor element 1100, and vice versa. As shown in FIG. 11, susceptor element 1100 may include susceptor element 1000 as shown in FIG. 10c (e.g., susceptor element 1000 having a pitch equal to approximately 5 wire diameters) and wire strand 1060. As further shown in FIG. 11, wire strand 1060 may have a pitch, p, based on how wire strand 1060 is wound with respect to susceptor element 1000. In the example shown in FIG. 11, p may be equal to approximately 12 wire diameters based on the diameter of wire strand 1060. In some non-limiting embodiments, wire strand 1060 may be made of the same material as one or more of the wire strands (e.g., one or more of first wire strand 1044, second wire strand 1046, third wire strand 1048, and fourth wire strand 1050) of susceptor element 1000. In some non-limiting embodiments, wire strand 1060 may be made of a different material than one or more of the wire strands of susceptor element 1000.

Figure 12:
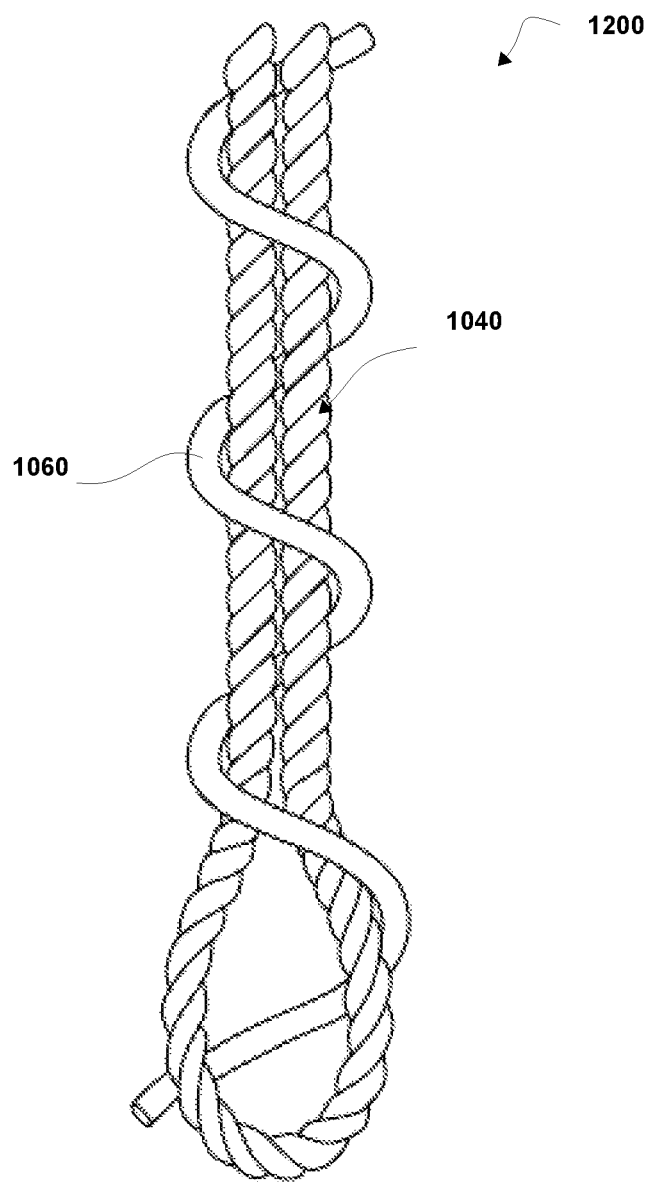
FIG. 12 is a diagram of a non-limiting embodiment of a susceptor element according to the present disclosure.

Referring now to FIG. 12, FIG. 12 is a diagram of susceptor element 1200. In some non-limiting embodiments, susceptor element 304 may be the same or similar to susceptor element 1200, and vice versa. As shown in FIG. 12, susceptor element 1200 may include first wire segment 1040 of susceptor element 1000 as shown in FIG. 10c (e.g., first wire segment 1040 having a pitch equal to approximately 2 wire diameters) and wire strand 1060. As shown in FIG. 12, wire strand 1060 may have a pitch equal to approximately 12 wire diameters based on the diameter of wire strand 1060. In addition, first wire segment 1040 may have a shape of a loop and wire strand 1060 may be wound around a portion of the loop of first wire segment 1040.

Figure 13:
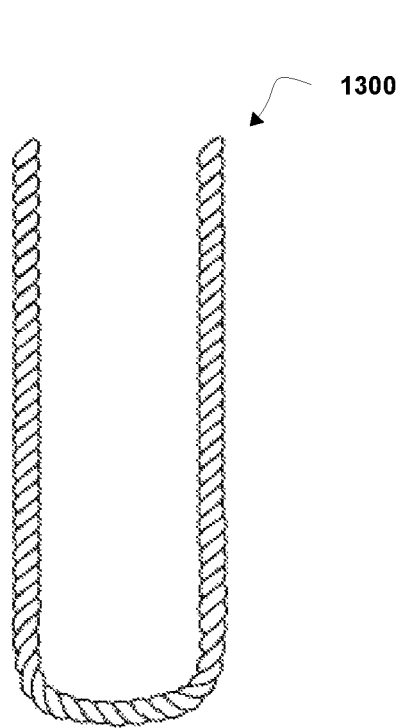
FIG. 13 is a diagram of a non-limiting embodiment of a susceptor element according to the present disclosure.

Referring now to FIG. 13, FIG. 13 is a diagram of susceptor element 1300. In some non-limiting embodiments, susceptor element 304 may be the same or similar to susceptor element 1300, and vice versa. As shown in FIG. 13, susceptor element 1300 may have a U-shape. In some non-limiting embodiments, susceptor element 1300 may be sized and configured so that susceptor element 1300 contacts an interior surface of an interior chamber of a cartridge (e.g., cartridge 302) based on the U-shape of susceptor element 1300 when susceptor element 1300 is placed within the cartridge.

Figure 14:
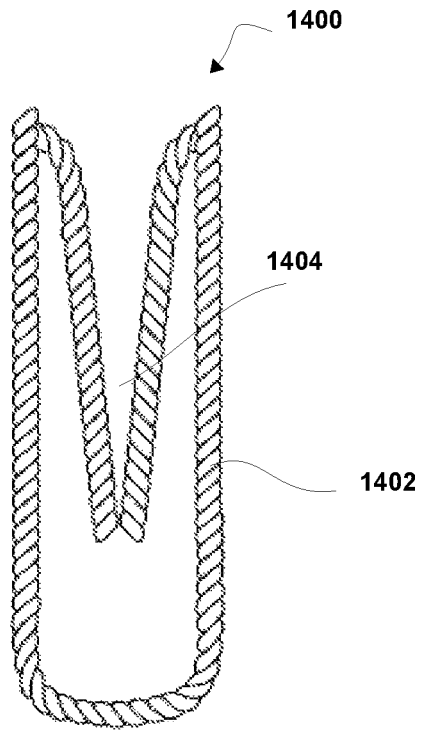
FIG. 14 is a diagram of a non-limiting embodiment of a susceptor element according to the present disclosure.

Referring now to FIG. 14, FIG. 14 is a diagram of susceptor element 1400. In some non-limiting embodiments, susceptor element 304 may be the same or similar to susceptor element 1400, and vice versa. As shown in FIG. 14, susceptor element 1400 may have U-shaped portion 1402 and V-shaped portion 1404 located within the U-shaped portion 1402. In some non-limiting embodiments, susceptor element 1400 may be sized and configured so that U-shaped portion 1402 of susceptor element 1400 contacts an interior surface of an interior chamber of a cartridge (e.g., cartridge 302) when susceptor element 1400 is placed within the cartridge. Additionally or alternatively, susceptor element 1400 may be sized and configured so that V-shaped portion 1404 of susceptor element 1400 is held in contact with a vaporizable substance located within the cartridge.

Figure 15:
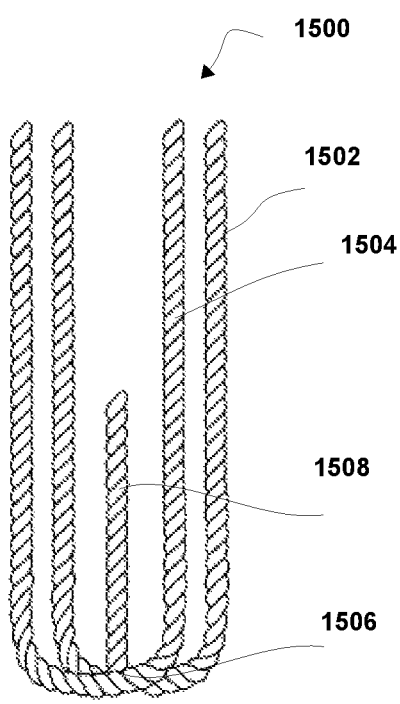
FIG. 15 is a diagram of a non-limiting embodiment of a susceptor element according to the present disclosure.

Referring now to FIG. 15, FIG. 15 is a diagram of susceptor element 1500. In some non-limiting embodiments, susceptor element 304 may be the same or similar to susceptor element 1500, and vice versa. As shown in FIG. 15, susceptor element 1500 may have first U-shaped portion 1502 and second U-shaped portion 1504 that are connected together at central point 1506. In addition, susceptor element 1500 may include center portion 1508 that is located centrally between first U-shaped portion 1502 and second U-shaped portion 1504. As further shown in FIG. 15, center portion 1508 may extend away from central point 1506. In some non-limiting embodiments, susceptor element 1500 may be sized and configured so that first U-shaped portion 1502 and second U-shaped portion 1504 of susceptor element 1500 contact an interior surface of an interior chamber of a cartridge (e.g., cartridge 302) when susceptor element 1500 is placed within the cartridge. Additionally or alternatively, susceptor element 1500 may be sized and configured so that center portion 1508 of susceptor element 1500 is held in contact with a vaporizable substance located within the cartridge.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. An electronic vaporizer device, comprising:
a cartridge configured to hold a vaporizable substance, the cartridge comprising:
a base section,
a side section coupled to the base section at a first end of the side section, wherein an aperture is defined at a second end of the side section,
wherein the side section comprises one or more apertures located in the side section, the one or more apertures being configured to allow air to flow into an interior of the cartridge when air flows out of the aperture defined at the second end,
wherein the base section and the side section define a fluid reservoir;
a susceptor element located within the cartridge; and
an induction heating element inductively coupled to the susceptor element and not in contact with the susceptor element,
wherein the one or more apertures comprises a first aperture and a second aperture,
wherein the first aperture is adjacent the second end of the side section and the second aperture is adjacent the first aperture,
wherein the second aperture is vertically offset and horizontally offset from the first aperture, and
wherein the first aperture is smaller than the second aperture.

2. The electronic vaporizer device of claim 1,
wherein the one or more apertures are configured to allow a volume of air into an interior chamber of the cartridge, and
wherein the volume of air is based on a volume per unit length of the cartridge.

3. The electronic vaporizer device of claim 1,
wherein the susceptor element comprises a plurality of wire strands that are wound together in a helical formation, and
wherein the wire strands comprise a ferromagnetic material.

4. The electronic vaporizer device of claim 1, wherein the cartridge has a cylindrical shape.

5. The electronic vaporizer device of claim 1,
wherein the one or more apertures comprises a plurality of slit apertures located in the side section, and
wherein a size of an opening of the plurality of slit apertures is greater at a location adjacent the base section of the cartridge than a size of the opening of the plurality of slit apertures adjacent the second end of the side section.

6. The electronic vaporizer device of claim 1, wherein the susceptor element comprises a wire having a coating of at least one of zirconia, silicon dioxide, or alumina.

7. The electronic vaporizer device of claim 1,
wherein the susceptor element comprises a plurality of wire strands,
wherein each wire strand has a same diameter, and
wherein the susceptor element has a pitch in a range of 25 wire diameters to 1 wire diameter.

8. The electronic vaporizer device of claim 1, wherein the cartridge is positioned such that the induction heating element surrounds at least a portion of the cartridge and surrounds at least a portion of the susceptor element.

9. The electronic vaporizer device of claim 8, further comprising:
a power source electrically connected to the induction heating element,
wherein the susceptor element is configured to heat a vaporizable substance located in the fluid reservoir based on induction heating of the susceptor element by the induction heating element,
wherein the susceptor element is located in the fluid reservoir and is further configured to transfer the vaporizable substance from the fluid reservoir based on a capillary action of the susceptor element,
wherein the induction heating element receives an alternating current from the power source and creates an electromagnetic field around the susceptor element, and
wherein the susceptor element generates heat based on the electromagnetic field.

10. The electronic vaporizer device of clan 1,
further comprising a shielding element,
wherein the shielding element is located within the cartridge, and
wherein the susceptor element is located within the shielding element.

11. The electronic vaporizer device of claim 10, wherein the shielding element surrounds a portion of the susceptor element when the susceptor element is located within the shielding element.

12. The electronic vaporizer device of claim 1,
wherein the one or more apertures comprises a third aperture,
wherein the third aperture is adjacent the second end of the side section and opposite the first aperture, and
wherein the third aperture is smaller than the second aperture.

13. The electronic vaporizer device of claim 12,
wherein the one or more apertures comprises a fourth aperture,
wherein the fourth aperture is adjacent the first aperture and the third aperture, and
wherein the fourth aperture is larger than the first aperture and the third aperture.

14. A cartridge assembly for containment of a vaporizable substance to be used in an electronic vaporizer device, the cartridge assembly comprising:
a cartridge comprising:
a base section,
a side section coupled to the base section at a first end of the side section, wherein an aperture is defined at a second end of the side section, and
wherein the side section comprises at least two apertures located in the side section, where the at least two apertures are configured to allow air to flow into an interior chamber of the cartridge when air flows out of the aperture defined at the second end, and
a susceptor element located within the cartridge,
wherein the at least two apertures comprise a first aperture and a second aperture,
wherein the first aperture is adjacent the second end of the side section and the second aperture is adjacent the first aperture,
wherein the second aperture is vertically offset and horizontally offset from the first aperture, and
wherein the first aperture is smaller thanthe second aperture.

15. The cartridge assembly of claim 14,
wherein the one or more apertures is configured to allow a volume of air into the interior chamber of the cartridge, and
wherein the volume of air is based on a volume per unit length of the cartridge.

16. The cartridge assembly of claim 14,
wherein the susceptor element comprises a plurality of wire strands that are wound together in a helical formation, and
wherein the wire is a ferromagnetic material.

17. The cartridge assembly of claim 14. wherein the susceptor element comprises a wire having a coating of at least one of zirconia, silicon dioxide, or alumina.

18. The cartridge assembly of claim 14,
further comprising a shielding element,
wherein the shielding element is located within the cartridge,
wherein the susceptor element is located within the shielding element,
wherein the susceptor element comprises a first ferromagnetic material and the shielding element comprises a second ferromagnetic material, and
wherein the first ferromagnetic material has greater ferromagnetic properties than the second ferromagnetic material.

* * * * *